US010414797B2

(12) United States Patent
Prades Cosano et al.

(10) Patent No.: US 10,414,797 B2
(45) Date of Patent: Sep. 17, 2019

(54) GELATINASE INHIBITORS AND USE THEREOF

(71) Applicant: Iproteos S.L, Barcelona (ES)

(72) Inventors: Roger Prades Cosano, Barcelona (ES); Jésus Seco Moral, Barcelona (ES); María Teresa Tarragó Clua, Barcelona (ES)

(73) Assignee: Iproteos S.L (ES)

( * ) Notice: Subject to any disclaimer, the term of this patent is extended or adjusted under 35 U.S.C. 154(b) by 0 days.

(21) Appl. No.: 15/776,296

(22) PCT Filed: Nov. 15, 2016

(86) PCT No.: PCT/EP2016/077632
§ 371 (c)(1),
(2) Date: May 15, 2018

(87) PCT Pub. No.: WO2017/085034
PCT Pub. Date: May 26, 2017

(65) Prior Publication Data
US 2018/0319839 A1 Nov. 8, 2018

(30) Foreign Application Priority Data
Nov. 16, 2015 (EP) .................... 15382567

(51) Int. Cl.
*A61K 38/02* (2006.01)
*C07K 5/097* (2006.01)
*C07K 5/08* (2006.01)
*C07K 5/103* (2006.01)
*C07K 7/06* (2006.01)
*C07K 5/107* (2006.01)
*A61K 38/00* (2006.01)

(52) U.S. Cl.
CPC .......... *C07K 5/0823* (2013.01); *C07K 5/0827* (2013.01); *C07K 5/1008* (2013.01); *C07K 5/1016* (2013.01); *C07K 7/06* (2013.01); *A61K 38/00* (2013.01)

(58) Field of Classification Search
None
See application file for complete search history.

(56) References Cited

U.S. PATENT DOCUMENTS 5,100,874 A 3/1992 Odake et al.
5,387,610 A 2/1995 Gray et al.

FOREIGN PATENT DOCUMENTS

| EP | 0345359 A1 | 12/1989 |
| WO | 9222523 A2 | 12/1992 |
| WO | 9815525 A1 | 4/1998 |
| WO | WO2009097893 | * 8/2009 |

OTHER PUBLICATIONS

Abdallah et al., "Amniotic Fluid MMP-9 and Neurotrophins in Autism Spectrum Disorders: An Exploratory Study", Autism Research, vol. 5, No. 6, Dec. 2012, pp. 428-433.
Abraham et al., "Inflammatory Bowel Disease", N Engl J Med, vol. 361, No. 21, Nov. 2009, pp. 2066-2078.
Agrawal et al., "Dystroglycan is Selectively Cleaved at the Parenchymal Basement Membrane at Sites of Leukocyte Extravasation in Experiemental Autoimmune Encephalomyelitis", Journal of Experimental Medicine, vol. 203, No. 4, Apr. 2006, pp. 1007-1019.
Bjorklund et al., "Gelatinase-Mediated Migration and Invasion of Cancer Cells", Biochimica et Biophysica Acta (BBA)—Reviews on Cancer, vol. 1755, No. 1, May 2005, pp. 37-69.
Chaturvedi et al., "MMP-9 Inhibition: A Therapeutic Strategy in Ischemic Stroke", Molecular Neurobiology, vol. 49, No. 1, Feb. 2014, pp. 563-573.
Coussens et al., "Matrix Metalloproteinase Inhibitors and Cancer: Trials and Tribulations", Science, vol. 295, No. 5564, Mar. 2002, pp. 2387-2392.
Demedts et al., "Matrix Metalloproteinases in Asthma and COPD", Current Opinion in Pharmacology, vol. 5, No. 3, Jun. 2005, pp. 257-263.
Di et al., "High Throughput Artificial Membrane Permeability Assay for Blood-Brain Barrier", European Journal of Medicinal Chemistry, vol. 38, No. 3, Mar. 2003, pp. 223-232.
Fragkouli et al, "Enhanced Neuronal Plasticity and Elevated Endogenous sAPPx Levels in Mice Over-Expressing MMP9", Journal of Neurochemistry, vol. 121, No. 2, Apr. 2012, pp. 239-251.
Gao et al., "Expression of Matrix Metalloproteinases-2 and -9 in Intestinal Tissue of Patients with Inflammatory Bowel Diseases", Digestive and Liver Disease, vol. 37, No. 8, Aug. 2005, pp. 584-592.
Garg et al., "Matrix Metalloproteinase-9-Mediated Tissue Injury Overrides the Protective Effect of Matrix Metalloproteinase-2 During Colitis", American Journal of Physiology-Gastrointestinal and Liver Physiology, vol. 262, No. 2, Feb. 2009, pp. G175-G184.
Gijbels et al., "Gelatinase B Is Present in the Cerebrospinal Fluid During Experimental Autoimmune Encephalomyelitis and Cleaves Myelin Basic Protein", Journal of Neuroscience Research, vol. 36, No. 4, Nov. 1993, pp. 432-440.

(Continued)

*Primary Examiner* — Satyanarayana R Gudibande
(74) *Attorney, Agent, or Firm* — Lerner, David, Littenberg, Krumholz & Mentlik, LLP

(57) ABSTRACT

New gelatinase inhibitors, processes for their preparation, pharmaceutical compositions comprising them, and their use in therapy and/or prophylaxis of conditions wherein inhibition of gelatinases is useful such as epilepsy, schizophrenia, Alzheimer disease, autism (in particular associated to fragile X syndrome), mental retardation, mood disorders such as bipolar disorders, depression, vascular diseases such as ischemic stroke and atherosclerosis, inflammatory diseases such as multiple sclerosis, rheumatoid arthritis and inflammatory bowel disease, drug addiction, neuropathic pain, lung diseases such as asthma and chronic obstructive pulmonary disease, cancer and sepsis.

17 Claims, No Drawings

(56) References Cited

OTHER PUBLICATIONS

Han et al., "The C(-1562)T Polymorphism of Matrix Meralloproteinase-9 Gene is Associated with Schizophrenia in China", Psychiatry Research, vol. 190, No. 1, Nov. 2011, pp. 163-164.
Hewson et al., "Suppression of Experimental Allergic Encephalomyelitis in the Lewis Rat by the Matrix Metalloproteinase Inhibitos Ro31-9790", Inflamm Res 44, May 1995, pp. 345-349.
International Search Report from PCT/EP2016/077632 dated Jan. 30, 2017.
Janssens et al., "What Has Been Learned About the Cardiovascular Effects of Matrix Metalloproteinases From Mouse Models?", Cardiovascular Research, vol. 69, No. 3, Feb. 2006, pp. 585-594.
Kansy et al., "Physicochemical High Throughput Screening: Parallel Artificial Membrane Permeation Assay in the Description of Passive Absorption Processes", Journal of Medicinal Chemistry, vol. 41, No. 7, Mar. 1998, pp. 1007-1010.
Kawasaki et al., "Distinct Roles of Matrix Metalloproteases in the Early- and Late- Phase Devlopment of Neuropathic Pain", Nature Medicine, vol. 14, No. 3, Mar. 2008, p. 331.
Kelly et al., "Increased Matrix Mealloproteinase-9 in the Airway After Allergen Challenge", American Journal of Respiratory and Critical Care Medicine, vol. 162, No. 3, Sep. 2000, pp. 1157-1161.
Kessenbrock et al., "Matrix Metalloproteinases: Regulators of the Tumor Microenvironment", Cell, vol. 141, No. 1, Apr. 2010, pp. 52-67.
Konopka et al., "Matrix Metalloproteinase-9 (MMP-9) in Human Intractable Epilepsy Caused by Focal Cortical Dysplasia", Epilepsy Research, vol. 104 (1-2), Mar. 2013, pp. 45-58.
Leigh et al., "A Randomized Double-Blind, Placebo-Controlled Trial of Minocyline in Children and Adolescents with Fragile X Syndrome", Journal of Developmental and Behavioral Pediatrics: JDBP, vol. 34, No. 3, Apr. 2013, p. 147.
Li et al., "Changes in Matrix Metalloproteinase-9 Levels During Progression of Atrial Fibrillation", Journal of International Medical Research, vol. 42, No. 1, Feb. 2014, pp. 224-230.
Li et al., "Increased Expression of Matrix Metalloproteinase 9 in Cortical Lesions from Patients with Focal Cortical Dysplasia Type IIb and Tuberous Sclerosis Complex", Brain Research, vol. 1453, May 2012, pp. 46-55.
Lindeman et al., "Clinical Trial of Doxycycline for Matrix Metalloproteinase-9 Inhibition in Patients With an Abdominal Aneurysm: Doxycycline Selectively Depletes Aortic Wall Neutrophils and Cytotoxic T Cells", Circulation, vol. 119, No. 16, Apr. 2009, pp. 2209-2216.
Matsumura et al., "Targeted Deletion or Pharmacological Inhibition of MMP-2 Prevents Cardiac Rupture After Myocardial Infarction in Mice", The Journal of Clinical Investigation, vol. 115, No. 3, Mar. 2005, pp. 599-609.

Mizoguchi et al., "Matrix Metalloprotease-9 Inhibition Improves Amyloid B-Mediated Cognitive Impairment and Neurotoxicity in Mice", Journal of Pharmacology and Experimental Therapeutics, vol. 331, No. 1, Oct. 2009, pp. 14-22.
Newman et al., "Identification of Matrix Metalloproteinases 3 (Stromelysin-1) and 9 (Gelatinase B) in Abdominal Aortic Aneurysm", Arteriosclerosis, Thrombosis, and Vascular Biology, vol. 14, No. 8, Aug. 1994, pp. 1315-1320.
Odake, S., et al., "Vertebrate Collagenase Inhibitor. I. Tripeptidyl Hydroxamic Acids," Chemical and Pharmaceutical Bulletin, Pharmaceutical Society of Japan, vol. 38, No. 4, Apr. 1, 1990, pp. 1007-1011, XP008041883, ISSN: 0009-2363, the whole document.
Opdenakker et al., "Functional Roles and Therapeutic Targeting of Gelatinase B and Chemokines in Multiple Sclerosis", The Lancet Neurology, vol. 2, No. 12, Dec. 2003, pp. 747-756.
Rybakowski et al., "Increased Serum Matrix Metalloproteinase-9 (MMP-9) Levels in Young Patients During Bipolar Depression", Journal of Affective Disorders, vol. 146, No. 2, Apr. 2013, pp. 286-289.
Samochowiec et al., "Functional Polymorphism of Matrix Metalloproteinase-9 (MMP-9) Gene in Alcohol Dependence: Family and Case Control Study", Brain Research, vol. 1327, Apr. 2010, pp. 103-106.
Serra, P., et al., "MMP-2 selectivity in hydroxamate-type inhibitors," Current Medicinal Chemistry, vol. 19 No. 7, Jan. 1, 2012, pp. 1036-1064, XP009189849, ISSN: 1875-533X, the whole document.
Swarnakar Snehasikta, et al., "The gelatinases and their inhibitors: the structure-activity relationships, Matrix Metalloproteinase Inhibitors," vol. 103, Jan. 1, 2012, pp. 57-82, XP009189848, ISSN: 1023-294X, the whole document.
Tayebjee et al., "Matrix Metalloproteinases in Coronary Artery Disease: Clinical and Therapeutic Implications and Pethological Significance", Current Medicinal Chemistry, vol. 12, No. 8, Apr. 2005, pp. 917-925.
Whittaker, M., et al., "Design and Therapeutic Application of Matrix Metalloproteinase Inhibitors," Chemical Reviews, American Chemical Society, US, vol. 99, Sep. 8, 1999, pp. 2735-2776, XP002370773, ISSN: 0009-2665, D0I: 10.1021/CR9804543, the whole document.
Xie et al., "Relationship Between Expression of Matrix Metalloproteinase-9 and Adenylyl Cyclase-Associated Protein I in Chronic Obstructive Pulmonary Disease", Journal of International Medical Research, vol. 42, No. 6, Dec. 2014, pp. 1272-1284.
Yamamori et al., "Plasma Levels of Mature Brain-Derived Neurotrophic Factor (BDNF) and Matrix Metalloproteinase-9 (MMP-9) in Treatment-Resistant Schizophrenia Treated with Clozapine", Neuroscience Letters, Nov. 2013, vol. 556, pp. 37-41.
Yoshida et al., "Decreased Serum Levels of Mature Brain-Derived Neurotrophic Factor (BDNF), but Not Its Precursor proBDNF, in Patients with Major Depressive Disorder", PloS One, vol. 7, No. 8, Aug. 2012, p. e42676.

\* cited by examiner

GELATINASE INHIBITORS AND USE THEREOF

CROSS-REFERENCE TO RELATED APPLICATIONS

The present application is a national phase entry under 35 U.S.C. § 371 of International Application No. PCT/EP2016/077632, filed Nov. 15, 2016, published as International Publication No. WO 2017/085034 A1, which claims priority from European Patent Application No. 15382567.4, filed Nov. 16, 2015, all of which are incorporated herein by reference.

FIELD OF THE INVENTION

The present invention relates to gelatinase inhibitors, to processes for their preparation, to pharmaceutical compositions comprising them, and to their use in therapy and/or prophylaxis of conditions wherein inhibition of gelatinases is useful such as epilepsy, schizophrenia, Alzheimer disease, autism (in particular associated to fragile X syndrome), mental retardation, mood disorders such as bipolar disorders, depression, vascular diseases such as ischemic stroke and atherosclerosis, inflammatory diseases such as multiple sclerosis, rheumatoid arthritis, and inflammatory bowel disease, drug addiction, neuropathic pain, lung diseases such as asthma and chronic obstructive pulmonary disease, cancer and sepsis.

BACKGROUND

There are accumulated evidences that the extracellular matrix (ECM) not only acts as a support structure but also has considerable effects on neuronal development and regeneration, synaptic plasticity, neuronal excitability, and homeostatic regulations of network activity. Indeed, the ECM has a profound impact on network behavior, hence on physiological processes such as cognition. Gelatinases belong to the Matrixines family (MMPs), which is formed by zinc dependent endopeptidases capable to degrade ECM proteins as well as a large number of non-ECM proteins, such as growth factors, cytokines, chemokines, cell surface receptors, serine proteinase inhibitors and other MMPs. MMPs are either secreted or membrane bound proteases and play major physiological roles in reproduction, growth, development, angiogenesis, immune response, wound healing and brain physiology. There is enhanced expression of MMPs, in particular gelatinases (MMP-2 or gelatinase A and MMP-9 or gelatinase B), during numerous pathological conditions, including tumor progression, neurodegeneration, stroke, inflammation and viral infections.

Initial studies on gelatinase MMP-9 in the brain originally were focused on its possible role in a variety of pathological conditions with a degenerative component. More recently, MMP-9 has emerged as an important player in the brain physiology, especially as being a key molecule in the synaptic plasticity. These findings led to studies demonstrating a possible involvement of MMP-9 in neuropsychiatric conditions such as epilepsy, schizophrenia, Alzheimer disease, autism (in particular associated to fragile X syndrome), mental retardation, bipolar disorders, mood disorders such as bipolar disorders, depression and drug addiction.

Alterations in glutamate signaling, leading to aberrant synaptic plasticity, in schizophrenia have been described. MMP-9 has been shown to regulate glutamate receptors, and modulating physiological and morphological synaptic plasticity. By means of functional gene polymorphism, gene responsiveness to antipsychotics and blood plasma levels, MMP-9 has recently been related to schizophrenia. This disease involves impairments in perception and cognition, culminating in a triad of positive, negative, and cognitive symptoms that are believed to reflect modifications in neuronal circuitry, the perturbation of synaptic connectivity, and alterations in dendritic spines. Notably, chromosome region 20q11-13, where the MMP-9 gene is located, has been extensively studied in terms of psychiatric disorders and linked to schizophrenia. MMP-9 influences hippocampal and prefrontal cortical function and is an interesting candidate molecule that is potentially involved in schizophrenia, a condition in which prefrontal cortex impairment is one of the most common pathological findings. Furthermore, some of the target candidate proteins that are implicated in schizophrenia have functional connections with either MMP-9 or MMP-9-interacting proteins, such as brain derived neurotrophic factor (BDNF) and N-methyl-D-aspartate (NMDA) receptors, among others. Abnormal elevated MMP-9 levels have been found in plasma of schizophrenic patients as reported by several authors (Yamamori, H. et al., *Neurosci Lett.*, 2013, (556):37-41).

There are accumulating evidences of the involvement of MMPs in the pathogenesis of epilepsy. This disease is a brain disorder characterized by an enduring predisposition to generate epileptic seizures and by the neurobiological, cognitive, psychological, and social consequences of this condition. It has been demonstrated that prolonged seizures are related to high-serum MMP-9 levels. More importantly, recent studies in brain tissue obtained during epilepsy surgery reported increased MMP-9 immunoreactivity in epileptogenic lesions of focal cortical dysplasia (Konopka, A. et al., *Epilepsy Res.*, 2013, (1-2):45-58) and tuberous sclerosis (Li, S. et al., *Brain Res*, 2012, (1453):46-55) as well as in the epileptogenic cortical or hippocampal lesions of patients with temporal lobe epilepsy without underlying cytoarchitectonic abnormalities. Using an unbiased approach of antibody microarrays it has been found an elevated expression of MMP-1, -2, -3, -8, -10 and -13, in addition to MMP-9, in the tissue from patients with focal cortical dysplasia (Konopka, A. et al., *Epilepsy Res.*, 2013, (1-2):45-58). However, the expression of these proteinases was not as pronounced and/or not as consistent among patients as the expression of MMP-9. Among these other MMPs, especially striking was the upregulation of MMP-2 in adult patients.

Autism spectrum disorders (ASDs) are identified by a cluster of symptoms in three core domains: social interaction, language, and range of interests, but in most cases their etiology is unknown. Fragile X syndrome (FXS) is the leading genetic cause of autism since a large percentage of individuals with FXS (46%) are co-diagnosed with ASD. High plasma activity of MMP-9 has been reported in individuals with FXS (Leigh, M. J. et al., *J Dev Behav Pediatr*, 2013, (34):1849-1857), whereas elevated protein amounts of MMP-9 were detected in amniotic fluid from ASD mother (Abdallah, M. W. et al., *Autism Res*, 2012, (5):428-433). Therefore, a clear connection exists between high levels of MMP-9 and ADS.

MMP-9 has been implicated also in human drug addiction, bipolar disorder and depression. One link is provided due to analyses of MMP-9 gene polymorphism at C(-1562)T that is functional, as it results in higher or lower MMP-9 expression. It has been reported that frequently of this polymorphism differentiates between healthy subjects and patients suffering from either bipolar disorders or schizophrenia (Han, H. et al., *Psychiatry Res*, 2011, (190):163-

164). This polymorphism has been linked as well to alcohol addiction (Samochowiec A et al, *Brain Res,* 2010, 1327: 103-6). In addition to this, it has been found that MMP-9 gene polymorphism modulates prefrontal cognition in bipolar men. Increased MMP-9 levels in young patients during bipolar depression have been reported (Rybakowski, J. K., et al., *J Affect Disord,* 2013, (146):286-289). High levels of MMP-9 in plasma have been detected in depression, this serum levels correlate with the severity of the depression (Yoshida, T. et al., *PLoS One,* 2012, (7):e42676).

MMP-9 is also claimed to be linked to degenerative diseases such Alzheimer's disease (AD). It has been shown that MMP participates in the formation and clearance of the Aβ peptides in AD. In fact, increased levels of MMP-9 have been observed in the brain tissue and blood of patients with AD, in particular in reactive astrocytes surrounding amyloid plaques, suggesting a local tissue response to plaque accumulation. Several studies have documented that this metalloproteinase participates in Aβ catabolism in vitro and in vivo and it is the only enzyme capable of degrading Aβ fibrils in vitro and Aβ plaques in situ. In addition, it has been reported that MMP-9 is involved in receptor-mediated sAPP-α release and exhibits a α-secretase-like activity in the brain in vivo (Fragkouli, A., et al., *J Neurochem,* 2012, (121):239-251). Synthetic inhibitors of MMP-2/MMP-9 reduce Aβ-mediated neuronal death in primary cultures (Mizoguchi, H., et al., *J Pharmacol Exp Ther,* 2009, (331): 14-22). In the same study, GM60001 treatment was neuroprotective upon intracerebroventricular administration of Aβ and improved cognition in mice. Moreover, MMP-9 KO mice did not undergo the memory deficits induced by Aβ injections in wild-type mice.

MMP-9 has also been identified to be involved in process and disease conditions other than those related with synaptic plasticity. These conditions include vascular, lung and inflammatory diseases, and cancer. In this regard, MMP-9, and in a lesser extend MMP-2, have been linked to vascular diseases such as ischemic stroke and atherosclerosis, neuropathic pain, inflammatory diseases such as multiple sclerosis, rheumatoid arthritis, and inflammatory bowel disease, multiple sclerosis, sepsis, cancer, lung diseases such as asthma and chronic obstructive pulmonary disease.

Ischemic stroke is a consequence of a deficit of a blood supply (resulting from a local thrombosis or arterial embolism), producing a decreased tissue oxygenation and in consequence bioenergetics disturbances that may lead to cell death of both necrotic and apoptotic character. Restoration of blood circulation after temporary hypoperfusion results in a robust inflammatory response that may exacerbate the tissue damage. The accumulation of inflammatory cells is then responsible for the high levels of reactive oxygen and nitrogen species as well as proinflammatory cytokines in the ischemic tissue. A dramatic increase of MMP-9 at all levels of its expression and activity is a hallmark of stroke consequences. MMP-9 is involved in such post-stroke events as long-term plasticity, vascular reorganization and angiogenesis, immune response and inflammatory. Blocking the MMPs, MMP-9 in particular, including KO mice, has been demonstrated to be protective against ischemic stroke and its consequences (Chaturvedi, M., et al., *Mol. Neurobiol.,* 2014, (49):563-573)

Treatment of neuropathic pain, triggered by multiple insults to the nervous system, is a clinical challenge because the underlying mechanism of neuropathic pain development remains poorly understood. However, recent studies report that early- and late-phase neuropathic pain development in rats and mice after nerve injury require different MMP. After spinal nerve injury, MMP-9 shows a rapid and transient upregulation in injured dorsal root ganglion (DRG) primary sensory neurons consistent with an early phase of neuropathic pain, whereas MMP-2 shows delayed response in DRG satellite cells and spinal astrocytes consistent with a late phase of neuropathic pain. Intrathecal administration of MMP-9 inhibitors or TIMP-1, an endogenous tissue inhibitor of MMP-9, delay the development of mechanical allodynia (central pain sensitization following painful stimulation) the first days (<10) after the injury. However, the inhibition of MMP-9 has no effect on allodynia when given 10 days after brain injury, showing the critical role of MMP-9 in the early development of neuropathic pain. Compared to MMP-9, MMP-2 upregulation after spinal nerve injury shows a delayed pattern. Intrathecal administration of TIMP-2, an endogenous inhibitor of MMP-2, or small synthetic inhibitors of MMP-2 partly attenuates allodynia on day 1 after injury but almost completely block allodynia in the following ten days. This shows the involvement of MMP-2 in the late phase of neuropathic pain. (Kawasaki, Y., et al., *Nature Medicine,* 2008, (3):331-336).

During an inflammatory response, leukocyte traffic through tissue barriers, including basement barriers membranes, is only possible if these cells are equipped with enzymes that can remodel ECM. MMP are therefore crucial effector molecules of inflammatory cells. MMPs can act as switches or as delicate turners in acute and chronic inflammation, during autoimmune diseases, when triggered in vascular diseases and in the regenerative phase after inflammation. Thus, MMP biology is important in the definition, execution and resolution phases of acute and chronic inflammatory and ischemic processes and consequently, MMP inhibitors might interfere with these. MMP inhibitors have been tested in many animal models of acute and chronic inflammation, such endotoxin shock, multiple sclerosis and rheumatoid arthritis. Bacteraemia, septic and endotoxin shock are the most frequent causes of mortality in modern hospitals. Bacterial cell-wall constituents induce a systematic response by the activation of the toll-like receptors, leading to an excessive production of inflammatory cytokines and enzymes. Mice deficient in MMP-9 have an altered resistance bacterial induced toxicity, whereas mice deficient in protease inhibitors are more susceptible to endotoxin shock.

Multiple sclerosis is a multifactorial disease that is influenced by genetic predisposition, environmental factors and immunological effector mechanisms that damage the central nervous system. MMP-9 is an immune effector molecule in multiple sclerosis (Opdenakker, G., et al., *Lancet Neurol.,* 2003, (2):747-756). It functions in cell migration through connective tissues and vessel walls and damages the blood-brain barrier. It also lyses protein substrates, such as myelin proteins, cell-adhesion molecules, cytokines and chemokines that are relevant in multiple sclerosis and other neurological diseases. Evidences which supports a detrimental role of MMP-9 in inflammatory CNS damage has been obtained in animal models. Murine experimental autoimmune encephalomyelitis (EAE), a model for multiple sclerosis, both gelatinases MMP-2 and MMP-9, become upregulated during the development of the disease syndrome (Gijbels, k., et al., *J. Neurosci. Res.,* 1993, (36):432-440). Young MMP-9 deficient mice have resistance to the development of EAE. Double Mmp2/Mmp9-knockout mice are completely resistant against the development of EAE. Pharmacological inhibition of MMP activity improves the course of EAE in several studies that used MMP inhibitors (Hewson, A., et al., *Inflamm. Res.,* 1995, (44):345-349). The use of MMP inhibitors might be also useful in the therapy of rheumatoid arthritis. MPP-9 is involved in the degradation of collagen II during rheumatoid arthritis, leading to the exposure and release of immunodominant epitopes. In addition, MMPs are important for the migration of inflammatory leukocytes. This suggests that MMP inhibitors might be useful in the therapy of rheumatoid arthritis, a notion that has been confirmed in different animal models (Agrawal, S., et al., *J. Exp. Med.,* 2006, (203):1007-1019).

Atherosclerosis and related diseases, including myocardial infarction and stroke, have often been compared with chronic inflammatory diseases. This is based on histopathological findings such as the activation of foamy macrophages, the local production of cytokines and chemokines, and the involvement of MMPs. The use of animal models with genetically altered mice (both transgenic and knockout) has strengthened the view that MMPs are key players in vascular pathologies (Janssens, S., et al., *Cardiovsac. Res.,* 2006, (69):585-594 and Tayebjee, M. H., et al., *Curr. Med. Chem.,* 2005, (12):917-925). It has been reported that MMP-9 levels increase with the progression of idiopathic atrial fibrillation (Li, M. et al., *J. Int. Med. Res.,* 2014, (1):224-230) and is associated with the development of aortic aneurysms (Newman, K. M., et al., *Arteriosclerosis and thrombosis: a journal of vascular biology,* 1994, (8): 1315-1320). Inhibition of MMP-9 suppresses the growth of aortic aneurysms (Lindeman, J. H., et al., *Circulation,* 2009, (119):2209-2216). Sudden death after myocardial infarction can occur by cardiac rupture, a process in which MMPs are involved. In mouse studies, the critical role of gelatinases in balance with endogenous tissue inhibitors of metalloproteases (TIMPs) is demonstrated. Myocardial infarction could be reversed by treating mice with an oral inhibitor of MMP-2 (Matsumura, S., et al., *J. Clin. Invest.,* 2005, (115): 559-609).

MMP-9 has a key role in the pathogenesis of chronic inflammatory disease, including ulcerative colitis and Crohn's disease (Abraham, C., et al., *N Eng J Med.,* 2009, (361):2066-2078), and its upregulation in colonic tissues has been shown to coincide with active flares of inflammatory bowel disease in humans (Gao, Q., et al., *Dig Liver Dis.,* 2005, (37):584-592). In agreement with data from human specimens, it has been observed elevated MMP-2 and MMP-9 protein expression and activation in inflamed colonic tissue in mouse models of inflammatory bowel disease. Moreover, it has been shown that colitis is attenuated in MMP-9 knockout mice, as well as MMP-2 and MMP-9 double-knockout mice. Thus, concomitant inhibition of MMP-2 and MMP-9 is therapeutically effective in inflammatory bowel disease (Grag, P., et al., *Am J Physiol Gastrointest Liver Physiol.,* 2009, (284): 15353-15357).

Mortality in cancer is primarily because of failure to prevent metastasis. Emerging evidences has emphasized the role of MMPs in early aspects of cancer dissemination (Kessenbrock, K., et al., *Cell,* 2010, (141):52-67). Enzymes that degrade the ECM have long been viewed as essential for tumor progression. Tumor cells are envisioned to produce enzymes that destroy the matrix barriers surrounding the tumor, permitting invasion into surrounding connective tissues, entry and exit from blood vessels, and metastasis to distant organs. MMPs have the capacity to degrade all structural components of ECM. Moreover, MMPs are up-regulated in virtually all human and animal tumors as well as in most tumor cell lines (Coussens, L. M., et al., *Science,* 2002, (295):2387-2392). MMP-9 is linked to cancer invasion. Elevated levels of MMP-9 in tissue and blood are observed in cancer patients, thus making MMP-9 attractive targets for cancer therapy, since the ability of MMP-9 to degrade collagen and laminin correlates with its ability to regulate cell migration, increase angiogenesis and tumor growth (Bjorklund, M., et al., *Biochim Biophys Acta,* 2005, (1755):37-69).

In pathological lung conditions, MMPs and their physiological inhibitors (TIMPs) are abnormally over expressed and produced in the respiratory tract by a panel of different structural cells. Alternations in these biological activities have several dramatic effects in wound healing and cell trafficking. Deregulation of various MMPs by stimulated structural or inflammatory cells is thought to take part to pathophysiology of numerous lung diseases including asthma, chronic obstructive pulmonary disease (COPD), lung fibrosis and lung cancer (Demedts, I. K., et al., *Curr Opin Pharmacol,* 2005, (5):257-63). The inflammation process is characterized by the extracellular matrix remodeling and collagen deposition that in turns request increased levels of MMP-9 (Kelly, E. A., et al., *Am J Respir Crit Care Med,* 2000, (162):1157-1161). Selective inhibition of MMP-9 is thought to promote a therapeutic benefit in these associated chronic inflammatory lung diseases as it has been proven recently in the treatment of COPD (Xie, S. S., et al., *J Int Med Res,* 2014, (42):1272-1284).

According to these experimental evidences, there is an existing need of finding new compounds which would be potent inhibitors of MMP-2 and MMP-9 and would be selective with respect to other MMPs such as collagenases (MMP-1), stromlysins (MMP-3) and matrylisins (MMP-7).

BRIEF DESCRIPTION OF THE INVENTION

The inventors have successfully found that a family of compounds of formula (I) are capable of inhibiting gelatinases MMP-2 and MMP-9 with a high potency and are selective in relation to their capacity to inhibit other MMPs such as collagenases (MMP-1), stromelysins (MMP-3) and matrilysins (MMP-7). These two properties make the compounds of the present invention ideal candidates for use in the therapy of epilepsy, schizophrenia, Alzheimer disease, autism (in particular associated to fragile X syndrome), mental retardation, bipolar disorders, mood disorders such as bipolar disorders, depression, vascular diseases such as ischemic stroke and atherosclerosis, inflammatory diseases such as multiple sclerosis, rheumatoid arthritis, and inflammatory bowel disease, drug addiction, neuropathic pain, lung diseases such as asthma and chronic obstructive pulmonary disease, cancer and sepsis since as explained above MMP-2 and MMP-9 are known to be involved in said diseases and it is also known that selectivity is a desired property to reduce the level of secondary effects produced when non-selective gelatinase inhibitors are used.

Therefore, one aspect of the invention relates to compounds having the formula (I):

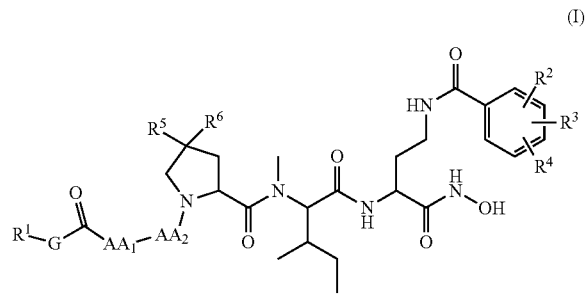

wherein

AA$_1$ is either absent or is a rest derived from an amino acid selected from the group consisting of N-methyl-phenylalanine, N-methyl-tryptophan, N-methyl-tyrosine and N-methyl-isoleucine, AA$_2$ is either absent or is a rest derived from an amino acid selected from the group consisting of N-methyl-phenylalanine, N-methyl-alanine, N-methyl-β-alanine and N-methyl-leucine, G is a linear or branched alkylene rest comprising from 1 to 10 carbon atoms wherein one or more non-vicinal methylene moieties (—CH$_2$—) in said rest may be replaced by corresponding oxygen atoms (—O—), R$^1$ is selected from the group consisting of hydrogen and phenyl, R$^2$, R$^3$ and R$^4$ are independently selected from the group consisting of hydrogen and fluorine, R$^5$ and R$^6$ are independently selected from the group consisting of hydrogen and fluorine, or a salt thereof.

Another aspect of this invention refers to processes for the preparation of a compound of formula (I) as defined above or a pharmaceutically acceptable salt, prodrug or solvate thereof.

Another aspect of this invention refers to pharmaceutical compositions comprising a compound of formula (I) as defined above, or a pharmaceutically acceptable salt, prodrug or solvate thereof and a pharmaceutically acceptable carrier, adjuvant or vehicle.

Another aspect of this invention refers to a compound of formula (I) as defined above, or a pharmaceutically acceptable salt thereof, for use as a medicament, particularly for the prevention and/or treatment of epilepsy, schizophrenia, Alzheimer disease, autism (in particular associated to fragile X syndrome), mental retardation, bipolar disorders, mood disorders such as bipolar disorders, depression, vascular diseases such as ischemic stroke and atherosclerosis, inflammatory diseases such as multiple sclerosis, rheumatoid arthritis, and inflammatory bowel disease, drug addiction, neuropathic pain, lung diseases such as asthma and chronic obstructive pulmonary disease, cancer and sepsis.

Another aspect of this invention refers to a method for the treatment or prevention of epilepsy, schizophrenia, Alzheimer disease, autism (in particular associated to fragile X syndrome), mental retardation, bipolar disorders, mood disorders such as bipolar disorders, depression, vascular diseases such as ischemic stroke and atherosclerosis, inflammatory diseases such as multiple sclerosis, rheumatoid arthritis, and inflammatory bowel disease, drug addiction, neuropathic pain, lung diseases such as asthma and chronic obstructive pulmonary disease, cancer and sepsis, preferably in a mammal, wherein a therapeutic amount of a compound of formula (I) as defined above, or a pharmaceutically acceptable salt, prodrug or solvate thereof, is administered to a patient in need of said treatment.

Another aspect of this invention refers to the use of a compound of formula (I) as defined above, or a pharmaceutically acceptable salt, prodrug or solvate thereof, for the preparation of a medicament, particularly for the prevention and/or treatment of a disease selected from the group consisting of epilepsy, schizophrenia, Alzheimer disease, autism (in particular associated to fragile X syndrome), mental retardation, bipolar disorders, mood disorders such as bipolar disorders, depression, vascular diseases such as ischemic stroke and atherosclerosis, inflammatory diseases such as multiple sclerosis, rheumatoid arthritis, and inflammatory bowel disease, drug addiction, neuropathic pain, lung diseases such as asthma and chronic obstructive pulmonary disease, cancer and sepsis.

DETAILED DESCRIPTION OF THE INVENTION

In the context of the present invention the term "rest derived from an amino acid" of formulae N(Me)H—R—COOH is to be understood as the biradical —N(Me)-R—CO—.

In the context of the present invention the term "alkylene" is used to designate a linear or branched hydrocarbon rest of formula —C$_n$H$_{2n}$—.

In the context of the present invention when, in an alkylene group, one or more non-vicinal methylenes (—CH$_2$—) are said to be replaced by corresponding oxygen atoms (—O—) it is meant that one or more of said methylenes is/are not present and its/their place is occupied by corresponding oxygen atom(s) forming and ether (—O—) link, with the proviso that two vicinal methylene groups may not be simultaneously replaced by oxygen atoms, i.e. the resulting chain may not contain a peroxide group (—O—O—). As a consequence the empirical formula of said modified alkylene rest will be C$_m$H$_{2m}$O$_x$. Non-limiting examples of said groups are n-propoxy, 1-[2-(2-ethoxy-ethoxy)-ethoxy]-propyl and 2-methoxy-ethoxymethyl.

In the context of the present invention when no steroisomery is indicated for an amino acid or amino acid rest it is to be understood that reference is made to any of the possible stereoisomers of said amino acid or amino acid rest. For example reference to isoleucine (Ile) includes D-Isoleucine and L-isoleucine.

In the context of the present invention some abbreviations and acronyms have been use and their meanings are provided below:

Alloc: Allyloxycarbonyl
Dab: 2,4-Diaminobutyric Acid
DBU: 1,8-Diazabicyclo[5.4.0]undec-7-ene
DCM: Dichloromethane
DIEA: N,N-Diisopropylethylamine
DMF: Dimethylformamide
DMSO: Dimethyl sulfoxide
DIC: N,N'-diisopropylcarbodiimide
EDC: 1-Ethyl-3-(3-dimethylaminopropyl)carbodiimide
Fmoc: Fluorenylmethyloxycarbonyl
HFIP: Hexafluoro-2-propanol or hexafluoroisopropanol
HOAt: 1-Hydroxy-7-azabenzotriazole
HPLC: High Performance Liquid Chromatography
HPLC-MS: High Performance Liquid Chromatography-mass spectrometry
MeOH: Methanol
Oxyma pure: ethyl cyano(hydroxyimino)acetate
PyBOP: Benzotriazol-1-yl-oxytripyrrolidinophosphonium hexafluorophos-phate
TBTU: O-(Benzotriazol-1-yl)-N,N,N',N'-tetramethyluronium tetrafluoro-borate
TFA: Trifluoroacetic acid
TIS: Triisopropylsilane
Tris: Tris(hydroxymethyl)aminomethane or 2-Amino-2-hydroxymethyl-propane-1,3-diol The term "salt" must be understood as any form of an active compound used in accordance with this invention in which said compound is in ionic form or is charged and coupled (associated) to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for the treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion, particularly when used on humans and/or mammals. These physiologically acceptable salts may also be formed with anions or acids and, in the context of this invention, are understood as being salts formed by at least one compound used in accordance with the invention— normally protonated, for example a protonated nitrogen— such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals.

Pharmaceutically acceptable acids include inorganic acids, such as hydrochloric, sulphuric, phosphoric, diphosphoric, hydrobromic, hydroiodic and nitrate acids, and organic acids, such as citric, maleic, malic, mandelic, ascorbic, oxalic, succinic, tartaric, acetic, methanesulfonic, ethanesulfonic, benzenesulfonic and p-toluenosulfonic acids. Pharmaceutically acceptable bases include hydroxides of alkali metals (e.g. sodium or potassium), alkaline-earth metals (for example, calcium or magnesium) and organic bases (for example, alkylamines, arylalkyilamines and heterocyclic amines).

Other preferred salts according to the invention are quaternary ammonium compounds in which an equivalent of an anion (X—) is associated with the positive charge of the N atom. X— may be an anion of diverse mineral acids such as for example, chloride, bromide, iodide, sulfate, nitrate, phosphate, or an anion of an organic acid, such as acetate, maleate, fumarate, citrate, oxalate, succinate, tartrate, malate, mandelate, trifluoracetate, methanesulfonate and p-toluenesulfonate. X— is preferably an anion selected from chloride, bromide, iodide, sulfate, nitrate, acetate, maleate, oxalate, succinate and trifluoracetate. More preferably X— is chloride, bromide, trifluoracetate or methanesulfonate.

The term "solvate" in accordance with this invention should be understood as meaning any form of the active compound in accordance with the invention in which said compound is bound by a non-covalent bond to another molecule (normally a polar solvent), including especially hydrates and alcoholates, like for example, methanolate. A preferred solvate is the hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald, J., Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The compounds of the present invention represented by the above described formula (I) may include enantiomers and/or diastereoisomers depending on the presence of chiral centers. The single isomers, enantiomers or diastereoisomers and mixtures thereof fall within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient, is capable of providing (directly or indirectly) a compound as described herein. However, it will be appreciated that non-pharmaceutically acceptable salts, solvates and prodrugs of the compounds of formula (I) also fall within the scope of the invention since those may be useful in the preparation of pharmaceutically acceptable salts, solvates and prodrugs of said compounds. The preparation of salts, solvates and prodrugs can be carried out by methods known in the art.

In one embodiment of the present invention the group $AA_1$ a rest derived from an amino acid selected from the group consisting of N-methyl-tryptophan and N-methyl-isoleucine.

In one embodiment of the present invention the groups $AA_1$ and $AA_2$ are absent.

In another embodiment of the present invention G is selected from the group consisting of —$CH_2$—, —$(CH_2)_3$—, —$(CH_2)_5$—, —$CH_2$—$CH(CH_3)$—$CH_2$—, —(CH$_2$)$_7$—, —CH$_2$—CH$_2$—CH$_2$—CH(CH$_2$—CH$_2$—CH$_3$)—, —O—(CH$_2$)$_3$—, —(CH$_2$)$_{13}$— and —CH$_2$—O—(CH$_2$)$_2$—O—CH$_2$—.

In another embodiment of the present invention R$^1$-G is selected from the group consisting of CH$_3$—, CH$_3$—(CH$_2$)$_2$—, CH$_3$—CH(CH$_3$)—CH$_2$—, CH$_3$—(CH$_2$)$_6$—, CH$_3$—(CH$_2$)$_4$—, CH$_3$—CH$_2$—CH$_2$—CH(CH$_2$—CH$_2$—CH$_3$)—, phenyl-O—(CH$_2$)$_3$—, CH$_3$—(CH$_2$)$_6$—O—(CH$_2$)$_3$— and —CH$_2$—O—(CH$_2$)$_2$—O—CH$_2$—.

In another embodiment of the present invention R$^1$-G is selected from the group consisting of CH$_3$—(CH$_2$)$_2$—, CH$_3$—CH(CH$_3$)—CH$_2$—, phenyl-O—(CH$_2$)$_3$—, CH$_3$—(CH$_2$)$_6$—, CH$_3$—(CH$_2$)$_4$— and CH$_3$—CH$_2$—CH$_2$—CH(CH$_3$—CH$_2$—CH$_3$)—. The compounds defined in this embodiment are particularly good at crossing the blood-brain barrier.

In another embodiment of the present invention one of R$^2$, R$^3$ and R$^4$ is hydrogen.

In another embodiment of the present invention one of R$^2$, R$^3$ and R$^4$ is hydrogen and the other two are fluorine atoms.

In another embodiment of the present invention the phenyl group substituted by R$^2$, R$^3$ and R$^4$ is a 3,5-difluorophenyl.

In another embodiment of the present invention R$^5$ and R$^6$ are both hydrogen.

In one embodiment of the present invention the compounds of formula (I) as hereinabove defined have the stereoisomery shown in the formula below:

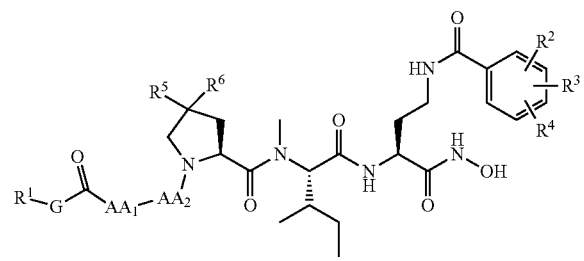

In additional preferred embodiments, the preferences described above for the different substituents are combined. The present invention is also directed to such combinations of preferred substitutions in the formulae above.

Particular individual compounds of the invention falling under formula (I) include the compounds listed below:
(2S)-1-acetyl-N-[(1S)-1-[[(1S)-3-[(4-fluorobenzoyl)amino]-1-(hydroxycarbamoyl)propyl]carbamoyl]-2-methyl-butyl]-N-methyl-pyrrolidine-2-carboxamide
(2S)-1-acetyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-1-hexanoyl-N-methyl-pyrrolidine-2-carboxamide
(2S)-1-butanoyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(3-methylbutanoyl)pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-octanoyl-pyrrolidine-2-carboxamide
(2S)—N-[(1S,2S)-1-[[(1S)-3-[(3,5-difluorobenzoyl)amino]-1-(hydroxycarbamoyl)propyl]carbamoyl]-2-methyl-butyl]-4,4-difluoro-1-hexanoyl-N-methyl-pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(2-propylpentanoyl)pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(4-phenoxybutanoyl)pyrrolidine-2-carboxamide
(2S)—N-[(1S)-1-[[(1S)-3-[(3,5-difluorobenzoyl)amino]-1-(hydroxycarbamoyl)propyl]carbamoyl]-2-methyl-butyl]-4,4-difluoro-N-methyl-1-(4-phenoxybutanoyl)pyrrolidine-2-carboxamide
(2S)-1-[(2S)-2-[acetyl(methyl)amino]-3-phenyl-propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)-1-[(2S)-2-[acetyl(methyl)amino]propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)-1-[3-[acetyl(methyl)amino]propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)-1-[(2S)-2-[[2-[butanoyl(methyl)amino]-3-(1H-indol-3-yl)propanoyl]-methyl-amino]-4-methyl-pentanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide
(2S)—N-[(1S)-1-[[(1S)-3-benzamido-1-(hydroxycarbamoyl)propyl]carbamoyl]-2-methyl-butyl]-N-methyl-1-hexanoyl-pyrrolidine-2-carboxamide
(2S,4R)—N-[(1S)-1-[[(1S)-3-benzamido-1-(hydroxycarbamoyl)propyl]carbamoyl]-2-methyl-butyl]-4-fluoro-N-methyl-1-pentanoyl-pyrrolidine-2-carboxamide or a pharmaceutically acceptable salt, isomer, prodrug or solvate thereof.

The compounds of formula (I) defined above can be obtained by available synthetic procedures as illustrated by the following general scheme:

Detailed Description of Routes of Synthesis of Compounds of Formula (I)

Alternative I:

A polymeric support suitable to be coupled to Nα-Fmoc-Nγ-Alloc-2,4-diaminobutyric acid (Fmoc-Dab(Alloc)-OH) through its carbonyl group and to yield upon cleavage a C-terminal carboxylic acid group, such as 2-Chlorotrityl resin (III), is placed in a syringe fitted with a polyethylene porous disk (reaction vessel). The resin is swelled by washes with appropriate organic solvents such as dichloromethane (DCM) and dimethylformamide (DMF).

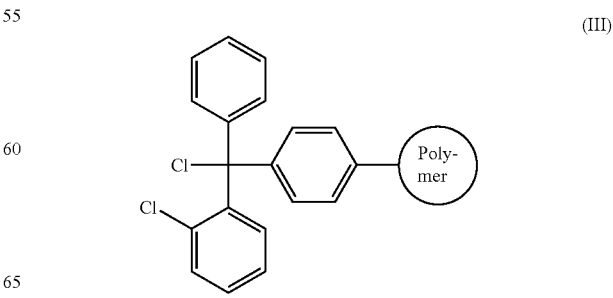

Following swelling of the polymeric support, Fmoc-Dab (Alloc)-OH is attached to the resin using an amine base such as N,N-Diisopropylethylamine (DIEA) in an appropriate organic solvent such as DMF. The mixture is stirred during 1 hour. After which, without filtering the mixture, anhydrous methanol is added to cap the remaining unreacted sites of the resin. After filtration and washing, Fmoc is removed to yield product of formula (IV) by a treatment with an amine base solution such as piperidine solution in DMF and/or a mixture of piperidine/DBU/toluene/DMF. Filtrates and washings are collected in a volumetric flask to quantify by UV measurements the achieved loading of the resin once the first amino acid is anchored. Fmoc removal is assessed also using the Kiser test.

using an activating agent such as benzotriazol-1-yl-oxytripyrrolidinophosphonium hexafluorophos-phate (PyBOP), in the presence or in the absence of an additive such as 1-hydroxy-7-azabenzotriazole (HOAt), and an amine base such as DIEA in an appropriate organic solvent such as DMF. The mixture is stirred during the total reaction time of 1 to 2 hours. The extent of the coupling may be monitored using the Kaiser test and re-coupling is done under the same conditions if required.

The Fmoc protecting group from the compound of formula (VI) is removed an amine base solution such as a piperidine solution in DMF and/or a mixture of piperidine/DBU/toluene/DMF to yield compound of formula (VIIa).

(IV)

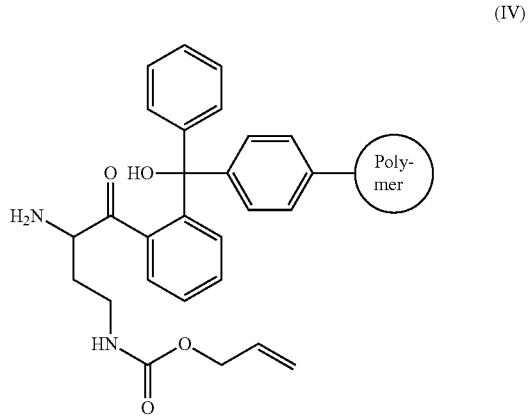 [SMILES: C=CCOC(=O)NCCC(N)C(=O)c1ccccc1C(O)(c1ccccc1)c1ccc(C)cc1]

A compound of formula (V):

(VIIa)

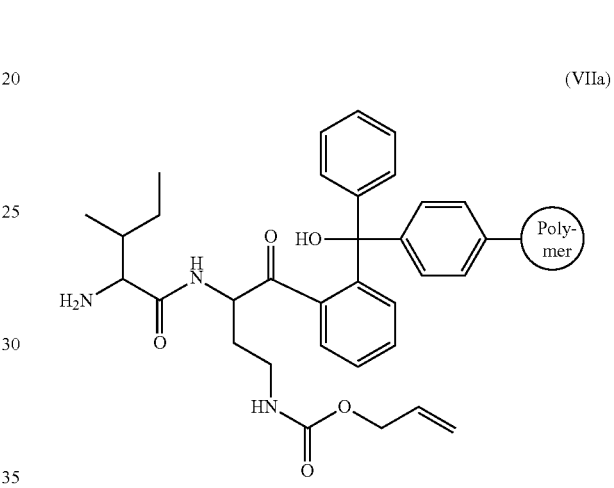

(V)

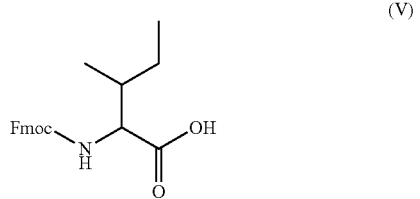

is attached to the compound of formula (IV) to yield the product of formula (VI)

Then the compound of formula (VIIa) is first reacted with an amino protecting group such as ortho-nitro benzene sulfonyl (oNBS) chloride to achieve a compound of formula (VIII).

(VIII)

(VI)

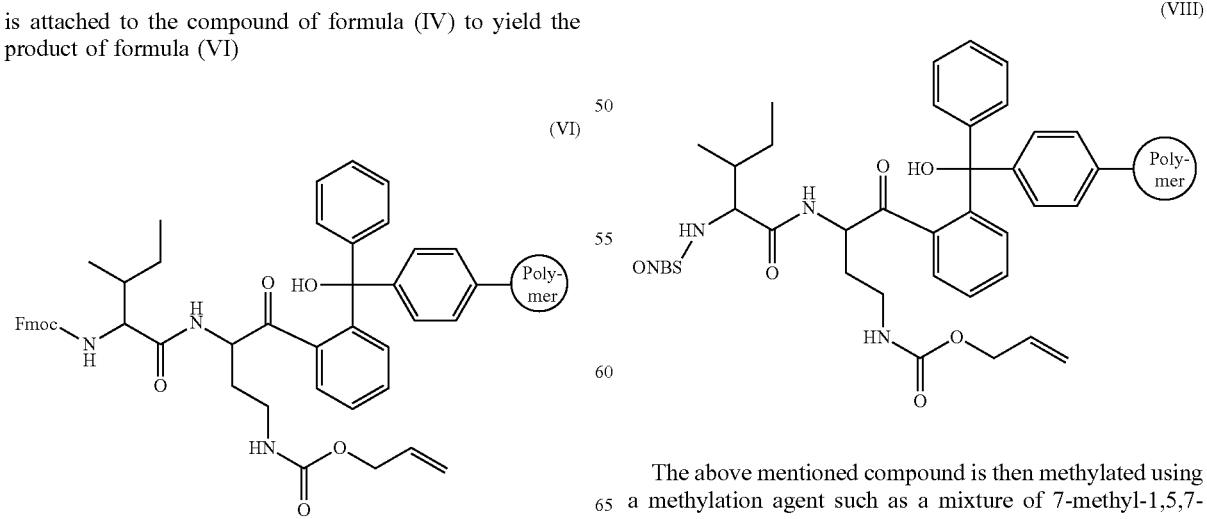

The above mentioned compound is then methylated using a methylation agent such as a mixture of 7-methyl-1,5,7-triazabicyclo[4.4.0]dec-5-ene and para-nitrobencenesulfonate to yield the product of formula (IX).

(IX)

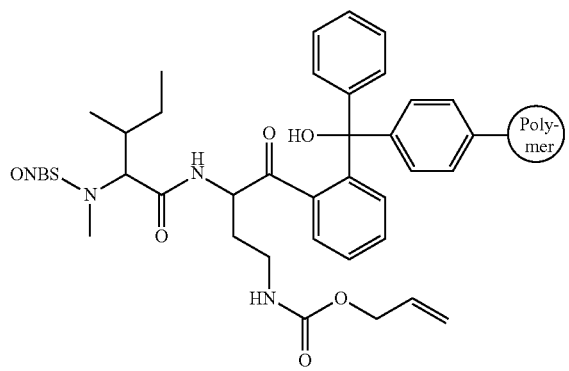

Subsequently the ortho-nitro benzene sulfonyl (oNBS) protecting group is removed by treating the resin with β-mercaptoethanol and DBU to yield the compound of formula (VII).

(VII)

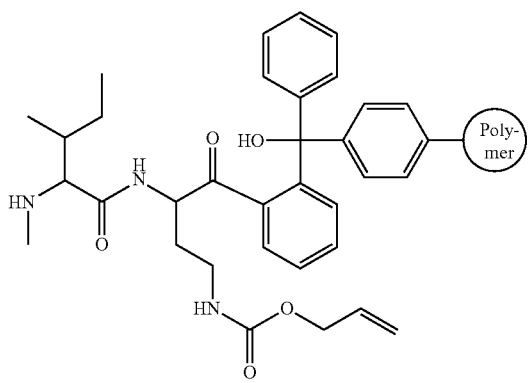

Once the compound of formula (V) has been coupled and methylated, the Fmoc-Proline-OH derivative of formula (X)

(X)

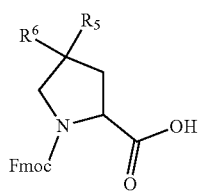

wherein $R^5$ and $R^6$ are as hereinabove defined is coupled to yield the product of formula (XI) using an activating agent such as PyBOP, in the presence or in the absence of an additive such as HOAt, and an amine base such as DIEA in an appropriate organic solvent such as DMF. The mixture is stirred during the total reaction time of 1 to 2 hours. The extent of the coupling may be monitored using the Kaiser test and re-coupling is done under the same conditions if required. The Fmoc protecting group from the Proline derivative of formula (X) is removed with an amine base solution such as a piperidine solution in DMF and/or a mixture of piperidine/DBU/toluene/DMF to yield a compound of formula (XI).

(XI)

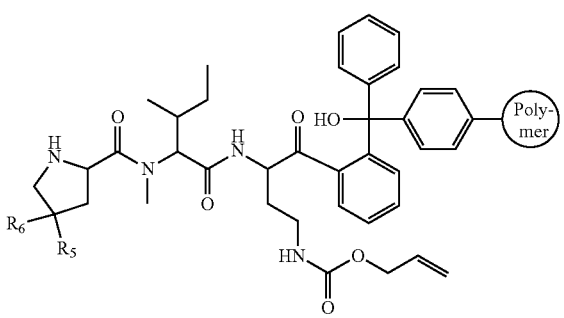

Fmoc-AA2-OH wherein AA2 is as herein above defined is anchored onto the product of formula (XI) to yield the product of formula (XII)

(XII)

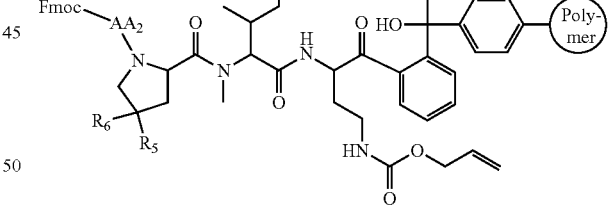

using an activating agent such as PyBOP, in the presence or in the absence of an additive such as HOAt, and an amine base such as DIEA in an appropriate organic solvent such as DMF. The mixture is stirred during the total reaction time of 1 to 2 hours. The extent of the coupling may be monitored using the chloranil test and re-coupling is done under the same conditions if required. The Fmoc protecting group from AA2 is removed with an amine base solution such as a piperidine solution in DMF and/or a mixture of piperidine/ DBU/toluene/DMF to yield a compound of formula (III).

(XIII)

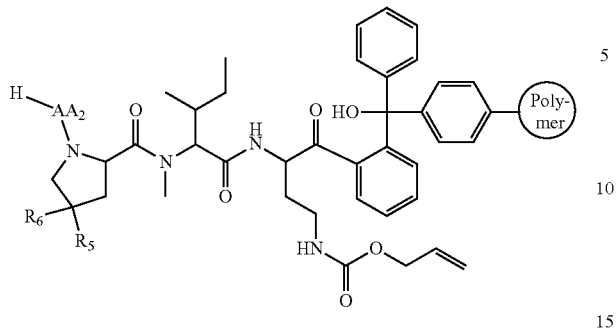

Fmoc-AA1-OH wherein AA1 is as herein above defined is attached onto the product of formula (XII) to yield the product of formula (XIV)

(XIV)

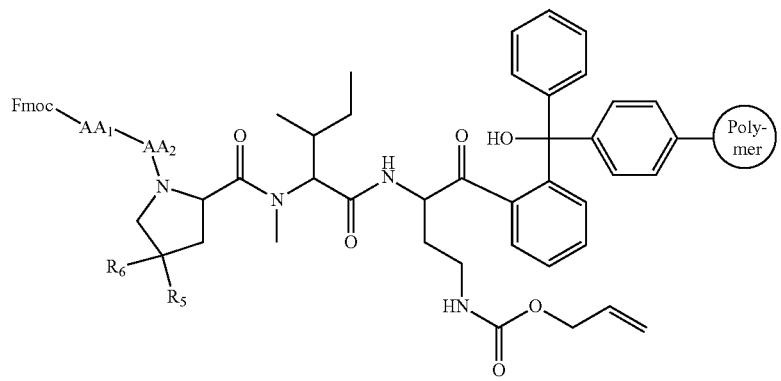

using an activating agent such as PyBOP, in the presence or in the absence of an additive such as HOAt, and an amine base such as DIEA in an appropriate organic solvent such as DMF. The mixture is stirred during the total reaction time of 1 to 2 hours. The extent of the coupling may be monitored using the Kaiser test and re-coupling is done under the same conditions if required. The Fmoc protecting group from AA1 is removed with an amine base solution such as a piperidine solution in DMF and/or a mixture of piperidine/DBU/toluene/DMF to yield a compound of formula (XV).

(XV)

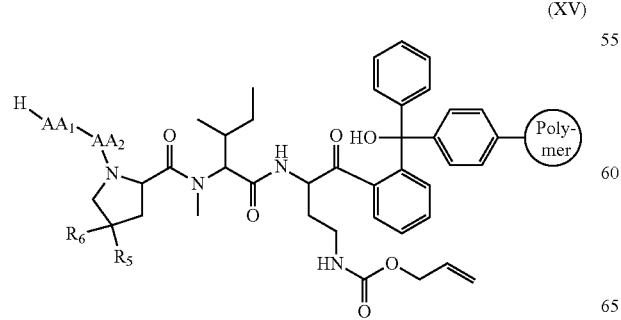

The amino group of the compound of formula (XV) is capped with group $R^1$-G-CO— to yield to compound of formula (XVI). Capping procedure is performed with an activated form of a carboxylic acid $R^1$-G-COOH such as an anhydride of formula $R^1$-G-CO—O—CO-G-$R^1$ or carbonyl halide of formula $R^1$-G-CO—X (wherein $R^1$ and G are as herein above defined and X is preferably Cl, Br or I) in the presence of an amine base such as DIEA in the presence or in the absence of an activating agent such as PyBOP, in the presence or in the absence of an additive such as HOAt. The extent of the reaction is monitored the kasier test.

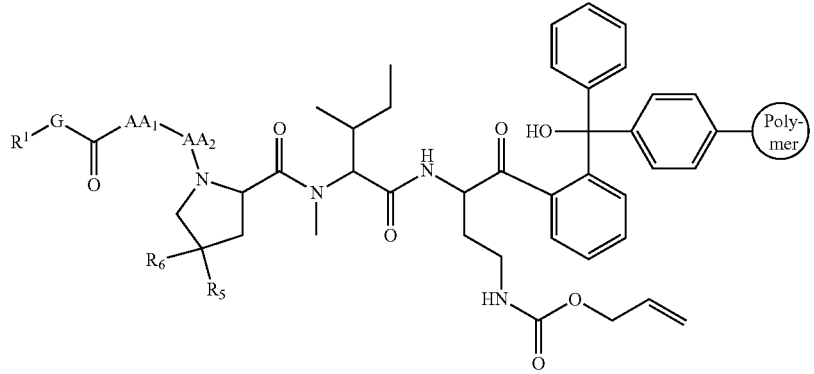

(XVI)

The alloc protecting group from the compound of formula (XVI) is removed to yield compound of formula (XVII) by suspending compound of formula (XVI) in an organic solvent such as DCM and adding phenylsilane to it, while $N_2$ is bubbled through the suspension. Then, tetrakis(triphenylphosphine)palladium(0) is added, and the $N_2$-bubbling maintained for 5 minutes. After that, the reaction vessel is sealed and shaken orbitally for 15 min. After this time, the reaction is filtered and the resin washed thoroughly. The same treatment is repeated two more times. After the last treatment, the resin is washed thoroughly with DCM, methanol (MeOH) and DMF. The extent of the removal of the alloc protecting group is monitored using the kasiser test.

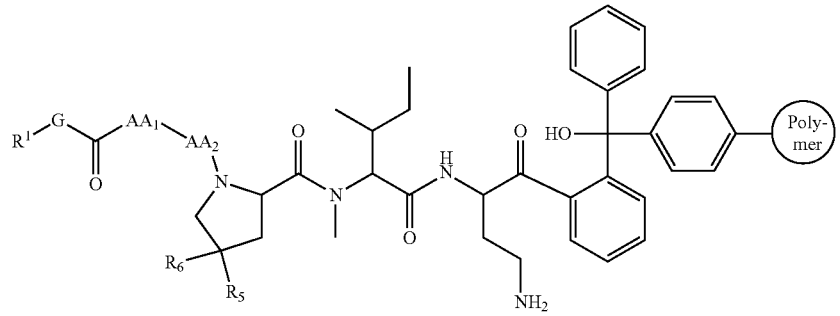

(XVII)

Subsequently, the product of formula (XVIII)

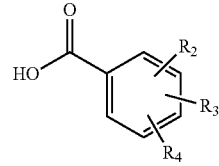

(XVIII)

wherein $R^2$, $R^3$ and $R^4$ are as hereinabove defined is coupled to the amino group of the side chain of the diaminobutiric acid moiety of compound of formula (XVII), using 3 eq of the compound of formula (XVIII), 3 eq of N,N'-Diisopropylcarbodiimide (DIPCDI) and 3 eq of HOAt in DMF. The mixture is intermittently stirred manually for 1 hour. Then the reaction mixture is filtered off and the resin is washed thoroughly with DMF, MeOH and DCM. The extent of the coupling reaction is monitored using the Kasiser test. A recoupling step of the compound of formula (XVIII) is carried out when the colorimetric test shows that the coupling reaction is not completely achieved. This step yields compound of formula (XIX)

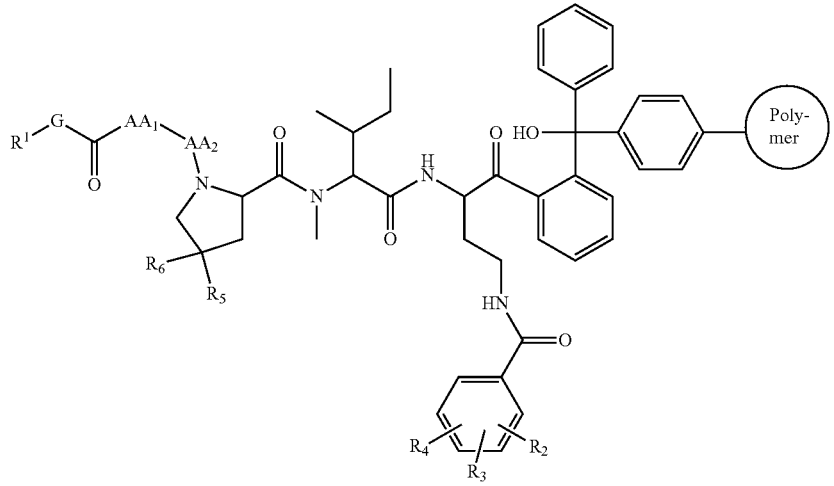

(XIX)

The compound of formula (XIX) is cleaved from the resin using hexafluoro-2-propanol (HFIP). The resin is washed several times with DCM and dried. Compound of formula (XX) is obtained by adding a HFIP/DCM (1:4) mixture to the compound of formula (XIX). The mixture is stirred at room temperature for 15 min. The reaction mixture is filtered and rinsed with HFIP/DCM and then DCM. The cleavage and washing step is repeated under the same conditions two additional times. After that, the filtrates obtained are pooled and the solvent is evaporated under vacuum to yield compound of formula (XX).

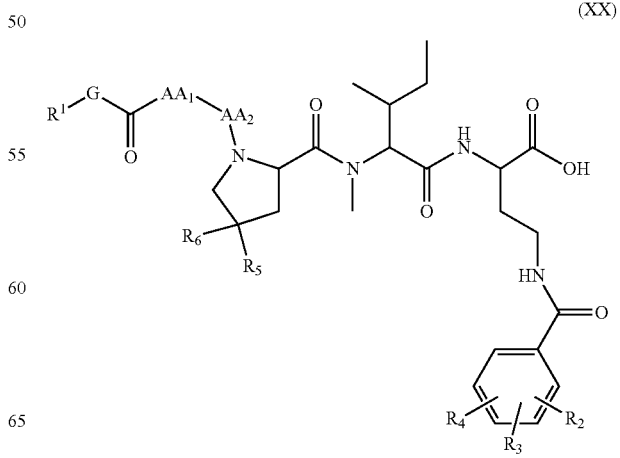

(XX)

The compound of formula (I) can be obtained from compound of formula (XX) by different procedures, below are shown the two procedures used for the synthesis of the examples:

Procedure A:

3.5 eq of the intermediate O-(2,4-dimethoxybenzyl)hydroxylamine are reacted with 1 eq of the compound of formula (XX) using 1.3 eq of 1-ethyl-3-(3-dimethylaminopropyl)carbodiimide hydrochloride (EDC.HCl) and 1.3 eq of the additive HOAt in the presence of 5 eq of an amine base such N-methylmorpholine in DCM or an equivalent organic solvent. The mixture is allowed to react for 20 hours at room temperature to yield compound of formula (XXI). The extent of the reaction is monitored using HPLC and HPLC-MS. Once the reaction is complete the reaction mixture is washed with $KHSO_4$, $NaHCO_3$ and brine (3 times each). The organic layer obtained is dried using magnesium sulfate, filtered and evaporated under vacuum.

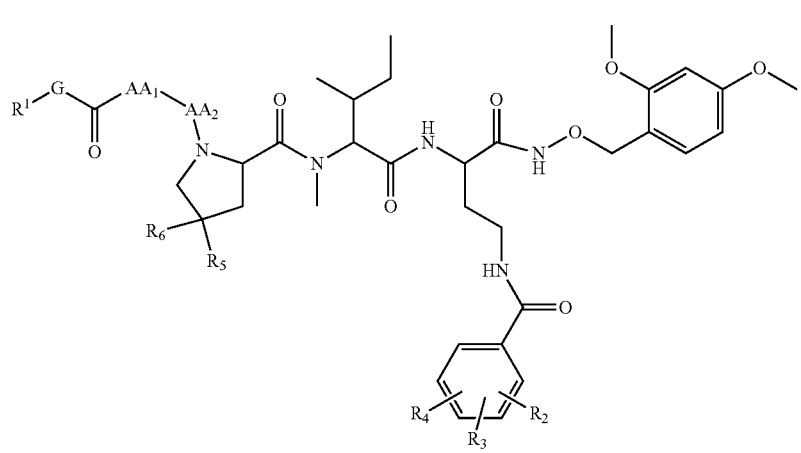

(XXI)

Finally, compound of formula (I) is obtained by treating compound of formula (XXI) with a mixture of trifluoroacetic acid (TFA)/water/triisopropylsilane (TIS) (95:2.5:2.5) for 1 hour. The completeness of the reaction is monitored using HPLC and HPLC-MS. The crude of compound of formula (I) is purified using HPLC when necessary.

Procedure B:

1 eq of the compound of formula (XX) is mixed with 1.1 eq of isobutyl chloroformate and 2.5 eq of a fresh prepared hydroxylamine solution (*) in the presence of an amine base such N-methylmorpholine in cool (−20° C.) dry tetrahydrofuran. The reaction is stirred for 2 hours at −20° C., letting the temperature reach 0° C. within 2 hours and then leaving it overnight at 5° C. The progress of the reaction is monitored by thin layer chromatography (TLC). Once completed, the solvent of the reaction is evaporated under vacuum to yield compound of formula (I). After which, the obtained crude is dissolved in ethyl acetate and washed with $KHSO_4$, $NaHCO_3$ and brine. Then the organic layer is dried with magnesium sulfate, filtered and evaporated.

(*) The hydroxylamine solution is prepared by dissolving 3 eq of hydroxylamine hydrochloride with 1 eq of KOH in MeOH at 0° C. The resulting mixture is stirred for 15 minutes at 0° C. KCl precipitates out and is removed by filtration. The resulting filtrate is used as such.

Alternative II:

A polymeric support suitable to be coupled to Fmoc-NH—OH through its alcohol group and to yield upon cleavage a hydroxamic acid group, such as 2-Chlorotrityl resin (III), is placed in a syringe fitted with a polyethylene porous disk (reaction vessel). The resin is swelled by washes with appropriate organic solvents such as dichloromethane (DCM) and dimethylformamide (DMF).

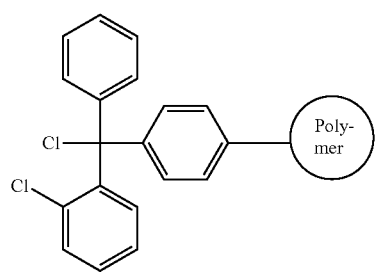

(III)

Following swelling of the polymeric support, Fmoc-NH—OH is attached to the resin using an amide base such as N,N-Diisopropylethylamine (DIEA) in an appropriate organic solvent such as DCM. The mixture is intermittently stirred during 24 h. After which, without filtering the mixture, anhydrous methanol is added to cap the remaining unreacted sites of the resin. After filtration and washing, Fmoc is removed to yield product of formula (XXII) by a treatment with an amine base solution such as piperidine in DMF and/or a mixture of piperidine/DBU/toluene/DMF. Filtrates and washings are collected in a volumetric flask to quantify by UV measurements the achieved loading of the resin once the linker is anchored to the polymeric support. Fmoc removal is assessed also using the Kiser test.

(XXII)

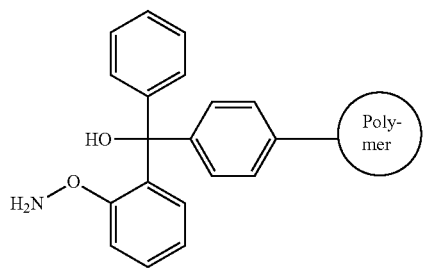

Nα-Fmoc-Nγ-Alloc-2,4-diaminobutyric acid (Fmoc-Dab(Alloc)-OH) is attached to the polymeric support of formula (XXII) to yield the product of formula (XXIII) using an coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the Kaiser test and re-coupling is done under the same conditions if required.

(XXIII)

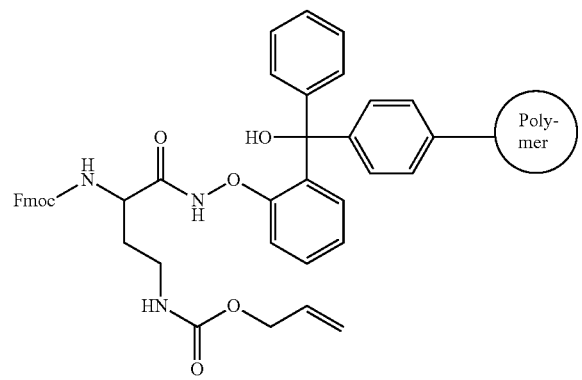

The Fmoc protecting group from the compound of formula (XXIII) is removed using an amine base solution such as a piperidine in DMF and/or a mixture of piperidine/DBU/toluene/DMF to yield compound of formula (XXIV).

(XXIV)

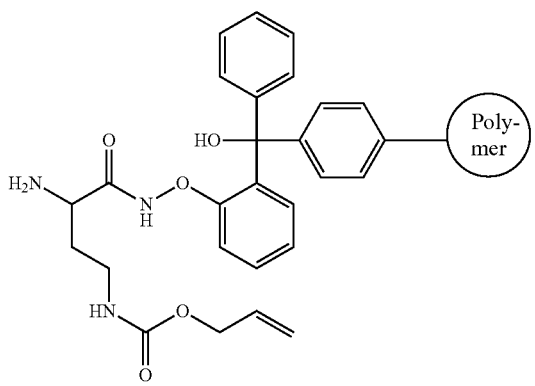

Nα-Fmoc-methyl isoleucine (Fmoc-NMeIle-OH) is attached to the compound of formula (XXIV) to yield the product of formula (XXV) using an activating agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the Kaiser test and re-coupling is done under the same conditions if required.

(XXV)

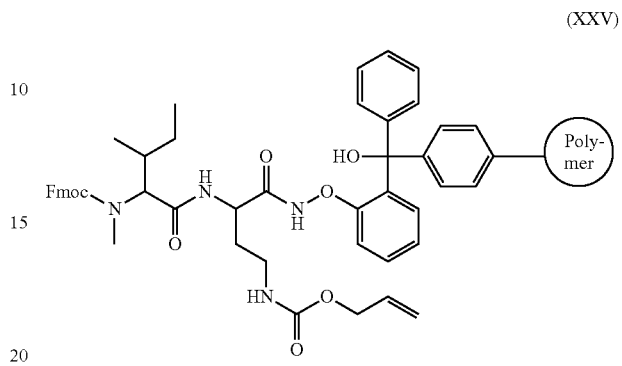

The Fmoc protecting group from the compound of formula (XXV) is removed an amine base solution such as a piperidine in DMF and/or a mixture of piperidine/DBU/toluene/DMF to yield compound of formula (XXVI).

(XXVI)

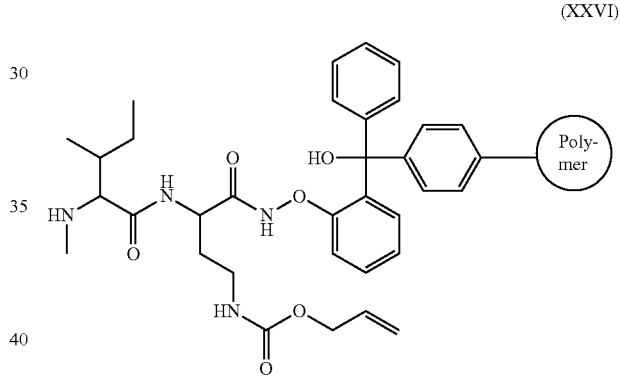

Once the compound of formula (XXVI) has been obtained, the Nα-Fmoc-Proline derivative of formula (X)

(X)

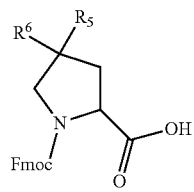

wherein $R^5$ and $R^6$ are as hereinabove defined is coupled to yield the product of formula (XXVII) using an coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the Kaiser test and re-coupling is done under the same conditions if required. The Fmoc protecting group from the compound of formula (X) is removed an amine base solution such as a piperidine in DMF and/or a mixture of piperidine/DBU/toluene/DMF to yield compound of formula (XXVII).

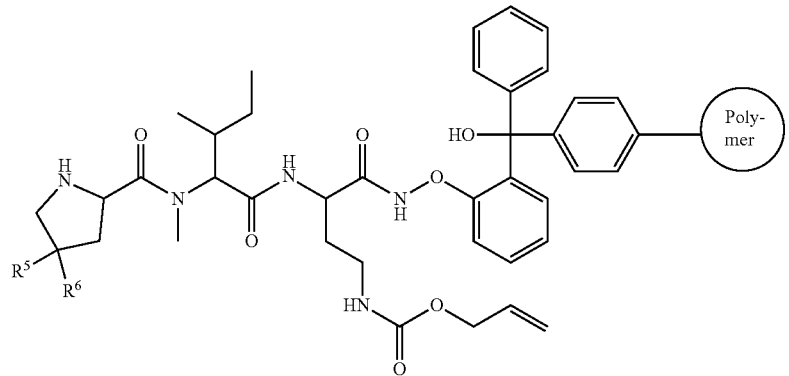

(XXVII)

Fmoc-AA$_2$-OH wherein AA$_2$ is as herein above defined is anchored onto the product of formula (XXVII) to yield the product of formula (XXVIII)

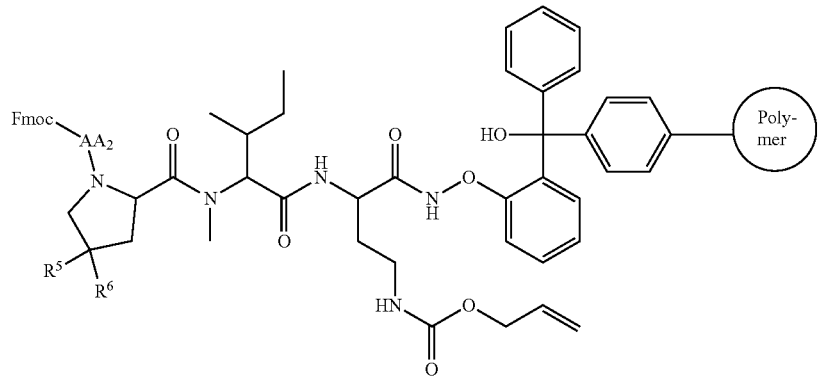

(XXVIII)

using coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the chloranil test and re-coupling is done under the same conditions if required. The Fmoc protecting group from AA$_2$ is removed with an amine base solution such as a piperidine in DMF and/or a mixture of piperidine/DBU/toluene/DMF to yield a compound of formula (XXIX).

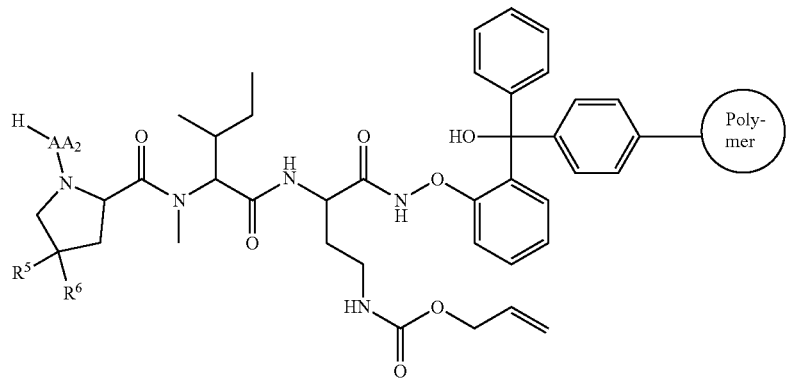

(XXIX)

Fmoc-AA$_1$-OH wherein AA$_1$ is as herein above defined is attached onto the product of formula (XXIX) to yield the product of formula (XXX)

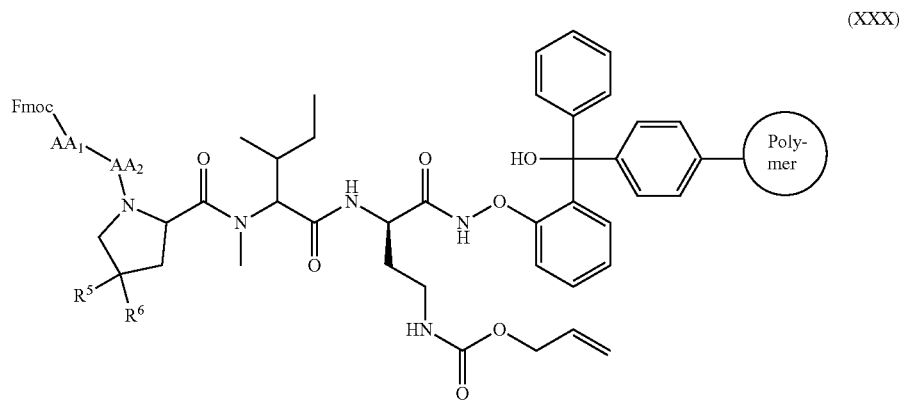

(XXX)

using a coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the Kaiser test and re-coupling is done under the same conditions if required. The Fmoc protecting group from the compound of formula (XXX) is removed an amine base solution such as a piperidine in DMF and/or a mixture of piperidine/DBU/toluene/DMF to yield compound of formula (XXXI).

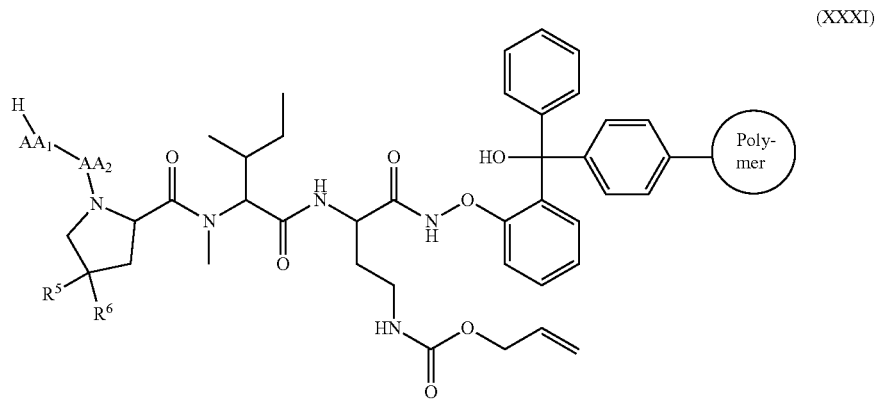

(XXXI)

The R$^1$-G- moiety wherein R$^1$ and G are as herein above defined is attached to the compound of formula (XXXI) using a coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. The extent of the coupling may be monitored using the Kaiser test and re-coupling is done under the same conditions if required to yield compound (XXXII).

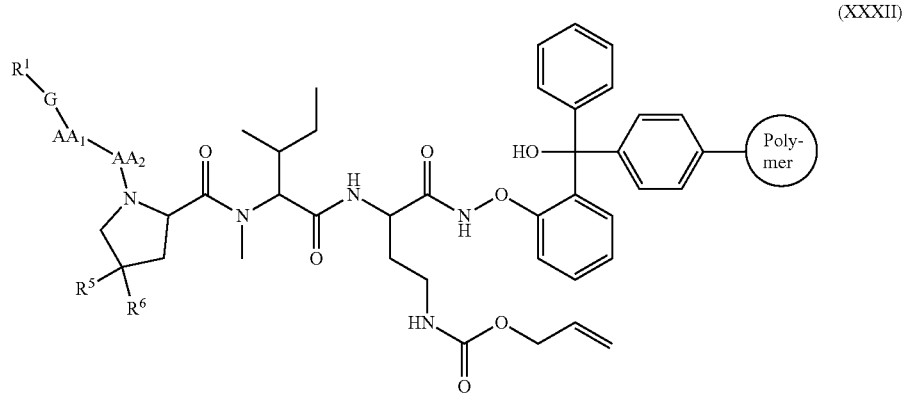

(XXXII)

The alloc protecting group from the compound of formula (XXXII) is removed to yield compound of formula (XXXIII) by suspending compound of formula (XXXII) in an organic solvent such as DCM and adding phenylsilane to it, while $N_2$ is bubbled through the suspension. Then, tetrakis(triphenylphosphine)palladium(0) is added, and the $N_2$-bubbling maintained for 5 minutes. After that, the reaction vessel is sealed and shaken orbitally for 15 min. After this time, the reaction is filtered and the resin washed thoroughly. The same treatment is repeated two more times. After the last treatment, the resin is washed thoroughly with DCM, MeOH and DMF. The extent of the removal of the alloc protecting group is monitored using the kasiser test.

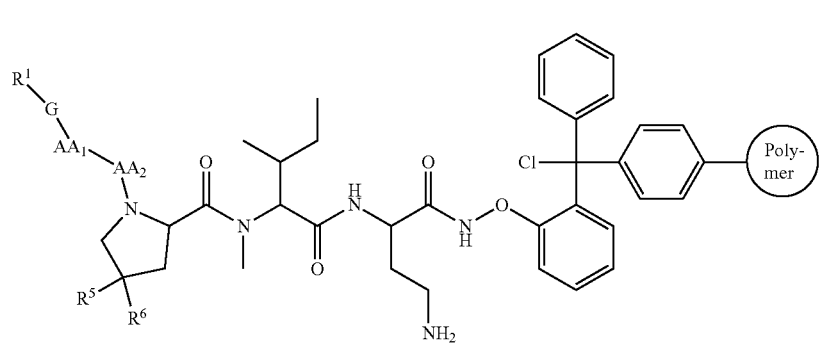

(XXXIII)

Subsequently, the product of formula (XVIII)

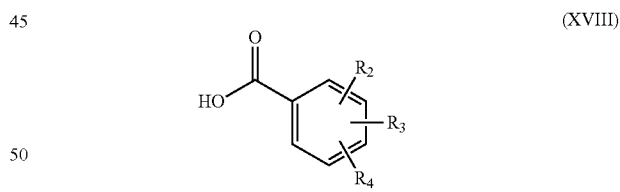

(XVIII)

wherein $R^2$, $R^3$ and $R^4$ are as hereinabove defined is coupled to the amino group of the side chain of the diaminobutiric acid moiety of compound (XXXIII), using a coupling agent such as N,N'-diisopropylcarbodiimide (DIC), in the presence or in the absence of an additive such as ethyl cyano(hydroxyimino)acetate (Oxyma pure) in an appropriate organic solvent such as DMF. The mixture is stirred during the total reaction time of 1 hour. Then the reaction mixture is filtered off and the resin is washed thoroughly with DMF, MeOH and DCM. The extent of the coupling reaction is monitored using the Kasiser test. A recoupling step of the compound of formula (XVIII) is carried out when the colorimetric test shows that the coupling reaction is not completely achieved. This step yields compound of formula (XXXIV).

(XXXIV)

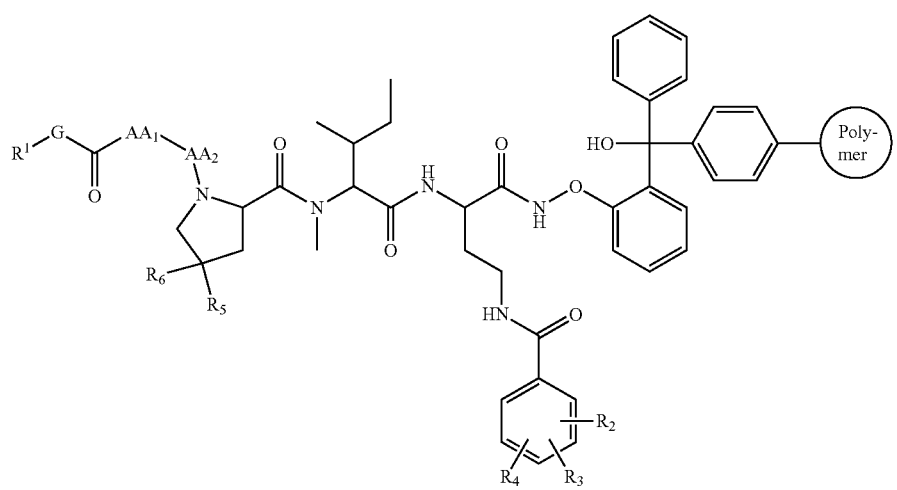

The compound of formula (XXXIV) is cleaved from the resin by adding an acid such as trifluoroacetic acid (TFA) in DCM (TFA/DCM 5:95). The mixture is stirred at room temperature for 15 min. After this time, the resin is filtered off and washed several times with TFA/DCM (5:95) and then DCM. After that the filtrates obtained are pooled and the solvent is evaporated under vacuum to yield compound of formula (I).

(I)

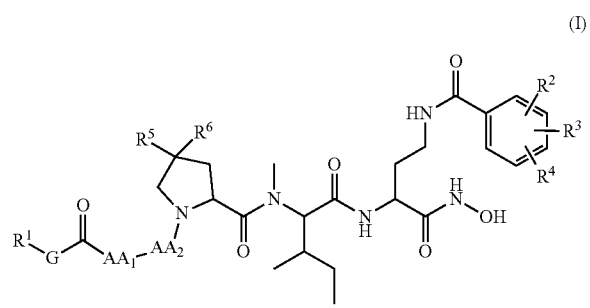

EXAMPLES

Example 1

(2S)-1-acetyl-N-[(1S)-1-[[(1S)-3-[(4-fluorobenzoyl)amino]-1-(hydroxycarbamoyl)propyl]carbamoyl]-2-methyl-butyl]-N-methyl-pyrrolidine-2-carboxamide

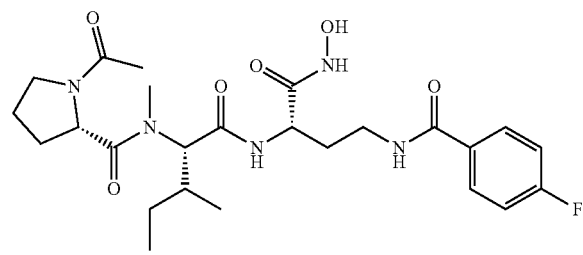 [SMILES: CCC(C)[C@@H](C(=O)N[C@@H](CCNC(=O)c1ccc(F)cc1)C(=O)NO)N(C)C(=O)[C@@H]1CCCN1C(C)=O]

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-L-isoleucine (Fmoc-L-Ile-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. Then, Fmoc-L-Pro-OH is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the removal of the Alloc group, 10 eq of phenylsilane in DCM are added to the resin while $N_2$ is bubbled through the mixture. Then, 0.1 eq of Pd(PPh$_3$)$_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 4-fluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 1. The compound is purified using reverse-phase chromatography.

Example 2

(2S)-1-acetyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

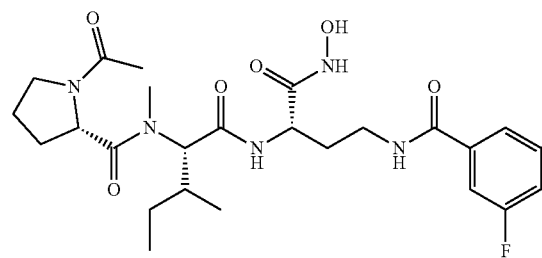

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. Then, Fmoc-L-Pro-OH is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the removal of the Alloc group, 10 eq of phenylsilane in DCM are added to the resin while $N_2$ is bubbled through the mixture. Then, 0.1 eq of Pd(PPh$_3$)$_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxyamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 2. The compound is purified using reverse-phase chromatography.

Example 3

(2S)—N-[(1S)-1-[[(1S)-3-[(3,5-difluorobenzoyl) amino]-1-(hydroxycarbamoyl)propyl]carbamoyl]-2-methyl-butyl]-1-hexanoyl-N-methyl-pyrrolidine-2-carboxamide

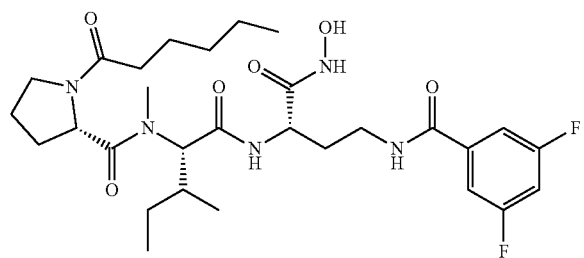 [SMILES: CCCCCC(=O)N1CCC[C@H]1C(=O)N(C)[C@H](C(=O)N[C@@H](CCNC(=O)c1cc(F)cc(F)c1)C(=O)NO)C(C)CC]

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. After that, the Fmoc-L-Pro-OH moiety is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Hexanoic acid is coupled to the Pro moiety by adding to the resin 20 eq of the acid, 10 eq of the coupling regent DPCDI and 10 eq of the additive HOAt. The reaction is stirred manually intermittently for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. A mixture of TFA/water/TIS (95:2.5:2.5) is added to the peptide crude and the mixture is lightly stirred during 2 hours. Afterwards, TFA is evaporated under a $N_2$ flow, yielding example 3. The compound is purified using reverse-phase chromatography.

Example 4

(2S)-1-butanoyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

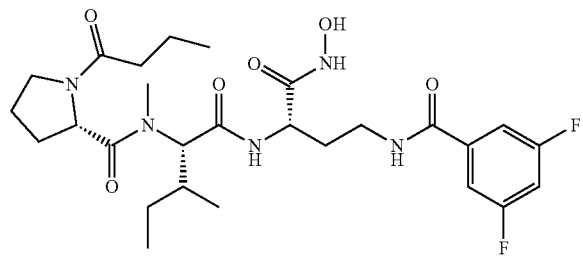 [SMILES: CCCC(=O)N1CCC[C@H]1C(=O)N(C)[C@H](C(=O)N[C@@H](CCNC(=O)c1cc(F)cc(F)c1)C(=O)NO)C(C)CC]

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of 3-mercaptoethanol and 5 eq of DBU (1×10' and 1×40'). The removal of the ortho-nitro benzene sulfonyl group is assessed using the chloranil test. After that, the Fmoc-L-Pro-OH moiety is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Hexanoic acid is coupled to the Pro moiety by adding to the resin 20 eq of the acid, 10 eq of the coupling regent DPCDI and 10 eq of the additive HOAt. The reaction is stirred manually intermittently for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. A mixture of TFA/water/TIS (95:2.5:2.5) is added to the peptide crude and the mixture is lightly stirred during 2 hours. Afterwards, TFA is evaporated under a $N_2$ flow, yielding example 4. The compound is purified using reverse-phase chromatography.

Example 5

(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(3-methylbutanoyl)pyrrolidine-2-carboxamide

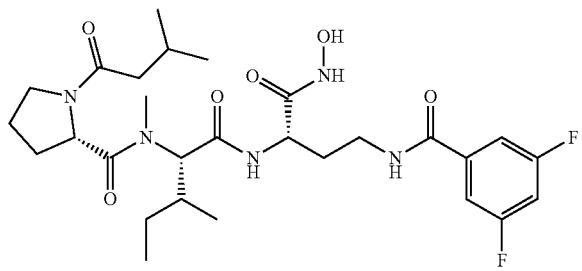 [SMILES: CCC(C)[C@@H](C(=O)N[C@@H](CCNC(=O)c1cc(F)cc(F)c1)C(=O)NO)N(C)C(=O)[C@@H]1CCCN1C(=O)CC(C)C]

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. After that, the Fmoc-L-Pro-OH moiety is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). 3-methylbutanoic acid is coupled to the Pro moiety by adding to the resin 20 eq of the acid, 10 eq of the coupling regent DPCDI and 10 eq of the additive HOAt. The reaction is stirred manually intermittently for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while N₂ is bubbled through the mixture. Then, 0.1 eq of Pd(PPh₃)₄ are added maintaining the N₂ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a N₂ atmosphere overnight. The extent of the reaction is monitored using HPLC. Once the desired product is obtained, the mixture is washed with 1N HCl, water and brine. The organic layer is dried over magnesium sulfate, filtered and evaporated. A mixture of TFA/water/TIS (95:2.5:2.5) is added to the peptide crude and the mixture is lightly stirred during 2 hours. Afterwards, TFA is evaporated under a N₂ flow, yielding example 5. The compound is purified using reverse-phase chromatography.

Example 6

(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-octanoyl-pyrrolidine-2-carboxamide

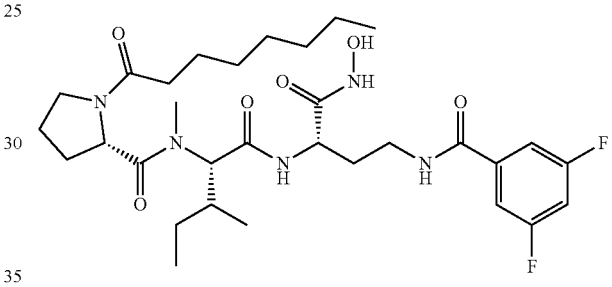

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. After that, the Fmoc-L-Pro-OH moiety is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Octanoic acid is coupled to the Pro moiety by adding to the resin 20 eq of the acid, 10 eq of the coupling regent DPCDI and 10 eq of the additive HOAt. The reaction is stirred manually intermittently for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of Pd(PPh$_3$)$_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. A mixture of TFA/water/TIS (95:2.5:2.5) is added to the peptide crude and the mixture is lightly stirred during 2 hours. Afterwards, TFA is evaporated under a $N_2$ flow, yielding example 6. The compound is purified using reverse-phase chromatography.

Example 7

(2S)—N-[(1S)-1-[[(1S)-3-[(3,5-difluorobenzoyl)amino]-1-(hydroxycarbamoyl)propyl]carbamoyl]-2-methyl-butyl]-4,4-difluoro-1-hexanoyl-N-methyl-pyrrolidine-2-carboxamide

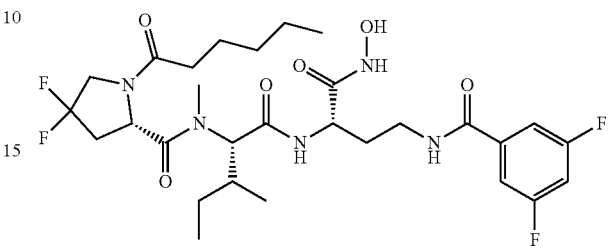

0.8 eq of commercially available Fmoc-L-Dab(Alloc)-OH and DIEA (4 eq) are added to the resin in 2 mL DMF. The mixture is intermittently stirred manually during 1 hour. After that, 0.5 mL/g of MeOH are added to the reaction mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Fmoc-L-Ile-OH, 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10' and 1×15'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. After that, the Fmoc-L-(4,4-difluoro)Pro-OH moiety is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Hexanoic acid is coupled to the Pro moiety by adding to the resin 20 eq of the acid, 10 eq of the coupling regent DPCDI and 10 eq of the additive HOAt. The reaction is stirred manually intermittently for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the Dab moiety, 3 eq of said acid, 3 eq of TBTU and 6 eq of DIEA in DMF are added to the resin. The reaction is allowed to react for 60 minutes. After this time, the resin is washed with DMF and DCM and the extent of the reaction is monitored the Kaiser test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. A mixture of TFA/water/TIS (95:2.5:2.5) is added to the peptide crude and the mixture is lightly stirred during 2 hours. Afterwards, TFA is evaporated under a $N_2$ flow, yielding example 7. The compound is purified using reverse-phase chromatography.

Example 8

(2S)—N-[(1S)-1-[[(1S)-3-[(3,5-difluorobenzoyl) amino]-1-(hydroxycarbamoyl)propyl]carbamoyl]-2-methyl-butyl]-N-methyl-1-(2-propylpentanoyl)pyrrolidine-2-carboxamide

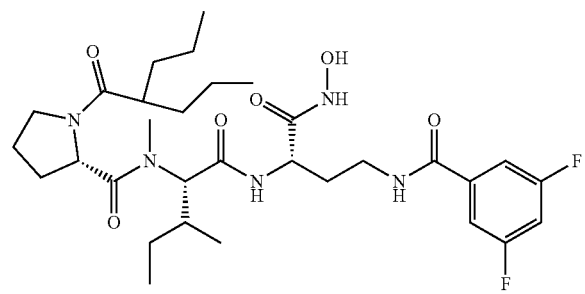 [SMILES: CCCC(CCC)C(=O)N1CCC[C@H]1C(=O)N(C)[C@H](C(=O)N[C@@H](CCNC(=O)c1cc(F)cc(F)c1)C(=O)NO)C(C)CC]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of the additive oxyma0 pure and dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). 2-propyl pentanoic acid is coupled to the proline moiety by adding to the resin 3 eq of the acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 8. The compound is purified using reverse-phase chromatography.

Example 9

(2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(4-phenoxybutanoyl)pyrrolidine-2-carboxamide

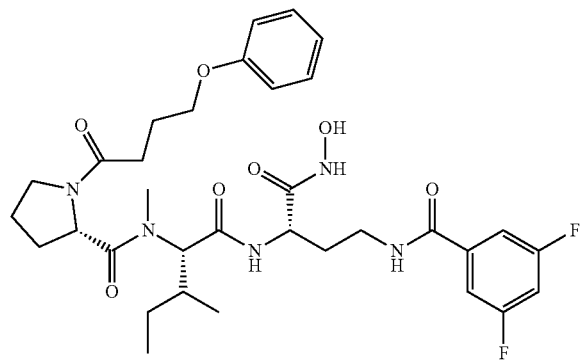 [SMILES: CCC(C)[C@@H](C(=O)N[C@@H](CCNC(=O)c1cc(F)cc(F)c1)C(=O)NO)N(C)C(=O)[C@@H]1CCCN1C(=O)CCCOc1ccccc1]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-L-NMeIle-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). 4-phenoxybutiric acid is coupled to the proline moiety by adding to the resin 3 eq of the acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 9. The compound is purified using reverse-phase chromatography.

Example 10

(2S)—N-[(1S)-1-[[(1S)-3-[(3,5-difluorobenzoyl)amino]-1-(hydroxycarbamoyl)propyl]carbamoyl]-2-methyl-butyl]-4,4-difluoro-N-methyl-1-(4-phenoxybutanoyl)pyrrolidine-2-carboxamide

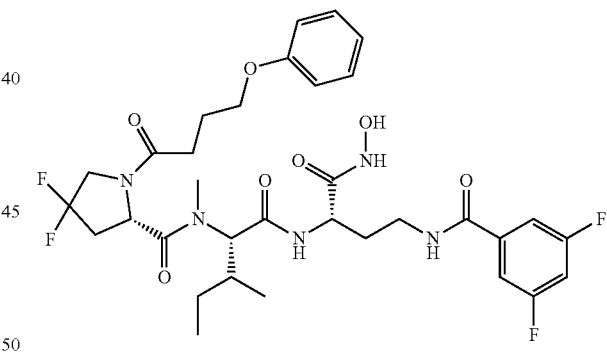

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-4,4-difluoro-L-Proline moiety is attached, for that purpose 3 eq of the amino acid, 3 eq of the coupling agent DIC and 3 eq of oxyma pure dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). 4-phenoxybutiric acid is coupled to the proline moiety by adding to the resin 3 eq of the acid, 3 eq of the coupling agent DIC and 3 eq of oxyma pure dissolved in a small amount of DMF and premixed for 2 minutes. The resulting the mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 10. The compound is purified using reverse-phase chromatography.

Example 11

(2 S)-1-[(2S)-2-[acetyl(methyl)amino]-3-phenyl-propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

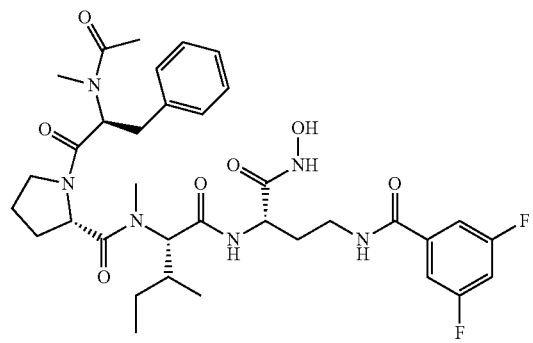 [SMILES: CCC(C)[C@@H](C(=O)N[C@@H](CCNC(=O)c1cc(F)cc(F)c1)C(=O)NO)N(C)C(=O)[C@@H]1CCCN1C(=O)[C@H](Cc1ccccc1)N(C)C(C)=O]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). After that, Fmoc-N-methyl-L-phenylalanine (Fmoc-NMe-L-Phe-OH) moiety is attached, for that purpose 3 eq of the amino acid, 3 eq of the coupling agent DIC and 3 eq of oxyma pure dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 11. The compound is purified using reverse-phase chromatography.

Example 12

(2 S)-1-[(2S)-2-[acetyl(methyl)amino]propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

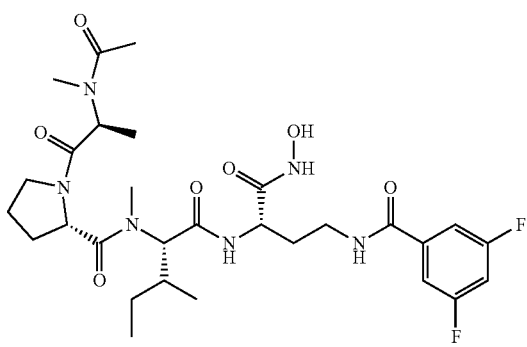 [SMILES: CCC(C)[C@@H](C(=O)N[C@@H](CCNC(=O)c1cc(F)cc(F)c1)C(=O)NO)N(C)C(=O)[C@@H]1CCCN1C(=O)[C@H](C)N(C)C(C)=O]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). After that, Fmoc-N-L-alanine (Fmoc-L-Ala-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the Ala amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 12. The compound is purified using reverse-phase chromatography.

Example 13

(2S)-1-[3-[acetyl(methyl)amino]propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

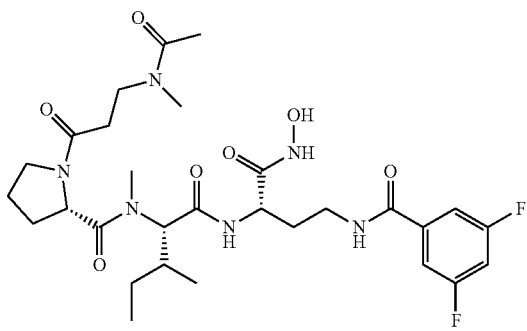 [SMILES: CCC(C)[C@@H](C(=O)N[C@@H](CCNC(=O)c1cc(F)cc(F)c1)C(=O)NO)N(C)C(=O)[C@@H]1CCCN1C(=O)CCN(C)C(C)=O]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). After that, Fmoc-3-alanine (Fmoc-β-Ala-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). The N-methylation of the amino group is achieved by treating the resin with 3 eq of 7-methyl-1,5,7-triazabicyclo[4.4.0]dec-5-ene and 4 eq of para-nitrobencensulfonate in DMF for 30 minutes (3 treatments). Between treatments the resin is washed thoroughly with DMF and DCM. After the N-methylation of the β-Ala amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the removal of the Alloc group, 10 eq of phenylsilane in DCM are added to the resin while N₂ is bubbled through the mixture. Then, 0.1 eq of Pd(PPh$_3$)$_4$ are added maintaining the N$_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 13. The compound is purified using reverse-phase chromatography.

Example 14

(2S)-1-[(2S)-2-[[(2S)-2-[butanoyl(methyl)amino]-3-(1H-indol-3-yl)propanoyl]-methyl-amino]-4-methyl-pentanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide

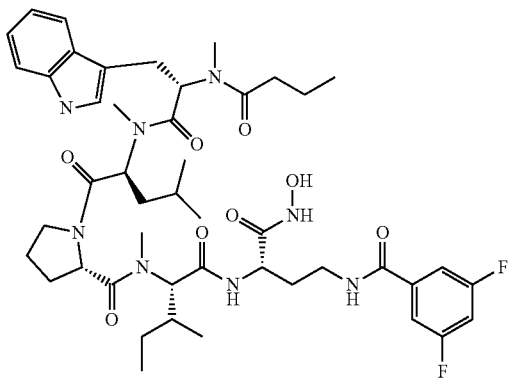 [SMILES: CCCC(=O)N(C)[C@@H](Cc1c[nH]c2ccccc12)C(=O)N(C)[C@@H](CC(C)C)C(=O)N1CCC[C@H]1C(=O)N(C)[C@H](C(=O)N[C@@H](CCNC(=O)c1cc(F)cc(F)c1)C(=O)NO)C(C)CC]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). After that, Fmoc-N-methyl-L-leucine (Fmoc-NMeLeu-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Nα-Fmoc-N(in)-Boc-N-methyl-L-tryptophan (Fmoc-NMe-L-Trp(Boc)-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). Butiric acid is coupled to the tryptophan moiety by adding to the resin 3 eq of the acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while N₂ is bubbled through the mixture. Then, 0.1 eq of Pd(PPh₃)₄ are added maintaining the N₂ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the 3,5-difluorobenzoic acid on the side chain of the diaminoethyl moiety, 3 eq of said acid, 3 eq of the coupling agent DIC and 3 eq of oxyma pure dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 14. The compound is purified using reverse-phase chromatography.

Example 15

(2S)—N-[(1S)-1-[[(1S)-3-benzamido-1-(hydroxycarbamoyl)propyl]carbamoyl]-2-methyl-butyl]-N-methyl-1-hexanoyl-pyrrolidine-2-carboxamide

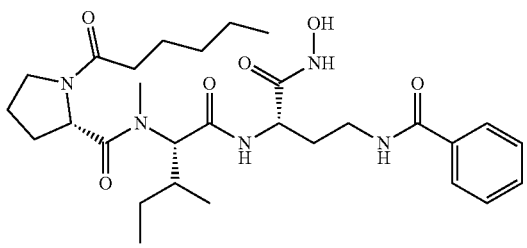 [SMILES: CCCCCC(=O)N1CCC[C@H]1C(=O)N(C)[C@H](C(=O)N[C@@H](CCNC(=O)c1ccccc1)C(=O)NO)C(C)CC]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-L-Proline (Fmoc-L-Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Hexanoic acid is coupled to the proline moiety by adding to the resin 3 eq of the acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of Pd(PPh$_3$)$_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the benzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 15. The compound is purified using reverse-phase chromatography.

Example 16

(2S,4R)—N-[(1S)-1-[[(1S)-3-benzamido-1-(hydroxycarbamoyl)propyl]carbamoyl]-2-methyl-butyl]-4-fluoro-N-methyl-1-hexanoyl-pyrrolidine-2-carboxamide

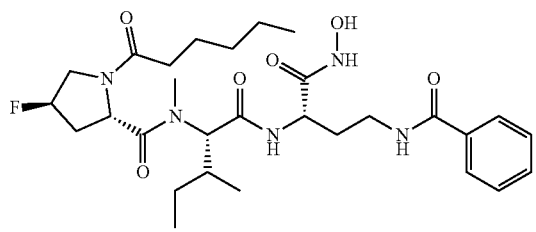 [SMILES: CCCCCC(=O)N1C[C@H](F)C[C@H]1C(=O)N(C)[C@H](C(=O)N[C@@H](CCNC(=O)c1ccccc1)C(=O)NO)C(C)CC]

1.5 eq of commercially available Fmoc-NH—OH and DIEA (10 eq) are added to the 2-chlorotrityl resin in 2 mL DCM. The mixture is intermittently stirred manually during 24 h. After that, 0.5 mL/g of MeOH are added to the reaction mixture to cap the remaining reactive points of the resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-Nγ-alloc-L-2,4-diaminobutyric acid (Fmoc-L-Dab(alloc)-OH), 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. To extent of the reaction is monitored using the Kaiser test. The Fmoc group is then removed by treatments with 20% piperidine in DMF (1×5', 1×10' and 1×15'). After that, Fmoc-N-methyl-L-isoleucine (Fmoc-NMe-L-Ile-OH) moiety is attached, for that purpose 3 eq of the amino acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15'). After that, Fmoc-trans-4-Fluoro-L-Proline (Fmoc-L-(F)Pro-OH) moiety is attached, for that purpose 3 eq of the amino acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). Hexanoic acid is coupled to the proline moiety by adding to the resin 3 eq of the acid, 3 eq of the coupling agent DIC and 3 eq of oxyma pure are dissolved in a small amount of DMF and premixed for 2 minutes. The resulting the mixture is added to the resin and the reaction is allowed to proceed for 60 minutes. Then the reaction is filtered off and the resin is rinsed thoroughly with DMF and DCM. The extent of the reaction is monitored using the chloranil test. For the removal of the Alloc group, 10 eq of phenylsilane in DCM are added to the resin while $N_2$ is bubbled through the mixture. Then, 0.1 eq of $Pd(PPh_3)_4$ are added maintaining the $N_2$ bubbling while mixing everything well. Then the reaction vessel is sealed and shaken for 15 minutes. After this time, the reaction is filtered and the resin washed thoroughly. The same treatment is repeated two more times. After the last treatment, the resin is washed thoroughly with DCM, MeOH and DMF. For the coupling of the benzoic acid on the side chain of the diaminoethyl moiety, 3 eq of said acid, 3 eq of the coupling agent DIC and 3 eq of oxyma pure are dissolved in a small amount of DMF and premixed for 2 minutes. The resulting mixture is added to the resin and the reaction is allowed to proceed for 60 minutes. After this time, the resin is washed with DMF and DCM and the extent of the reaction is monitored the Kaiser test.

For the cleavage of the peptide, the resin is washed several times with DCM and dried by suction. The peptide is cleaved from the resin by adding a solution of DCM/TFA (95:5), the mixture is allowed to react for 15 min. Then the reaction mixture is filtered and the resin rinsed with DCM. This cleavage procedure is repeated twice. All the filtrates are pooled and the solvent is evaporated under vacuum, yielding example 16. The compound is purified using reverse-phase chromatography.

Comparative Examples

Comparative Example 17

(2S)-2-[[(2S)-1-acetylpyrrolidine-2-carbonyl) amino]-N-[(1S)-2-(hydroxyamino)-1-(1H-indol-3-ylmethyl)-2-oxo-ethyl]pentanediamide

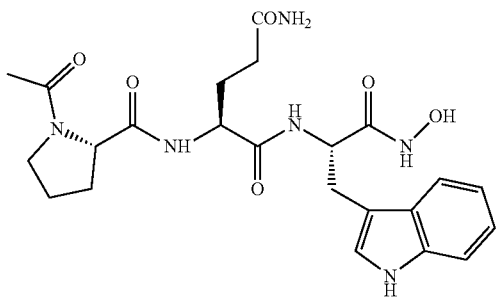 [SMILES: CC(=O)N1CCC[C@H]1C(=O)N[C@@H](CCC(N)=O)C(=O)N[C@@H](Cc1c[nH]c2ccccc12)C(=O)NO]

0.8 eq of commercially available Nα-Fmoc-N(in)-Boc-L-tryptophan (Fmoc-L-Trp(Boc)-OH), and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Nα-Fmoc-Nδ-trityl-L-glutamine (Fmoc-L-Gln(Trt)-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). The, Fmoc-L-Proline (Fmoc-L-Pro-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 17. The compound is purified using reverse-phase chromatography.

Comparative Example 18

(2 S)-2-acetamido-N-[(1S)-2-[[(1S)-1-(hydroxycarbamoyl)-2-methyl-butyl]amino]-1-(1H-indol-3-ylmethyl)-2-oxo-ethyl]pentanediamide

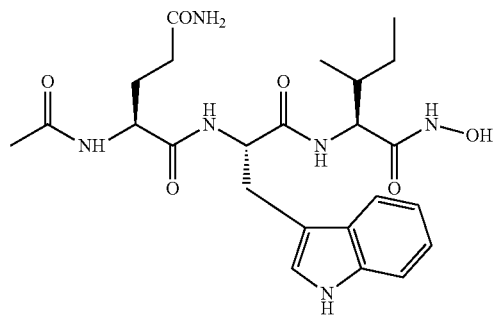 [SMILES: CCC(C)[C@H](NC(=O)[C@H](Cc1c[nH]c2ccccc12)NC(=O)[C@H](CCC(N)=O)NC(C)=O)C(=O)NO]

0.8 eq of commercially available Fmoc-L-isoleucine (Fmoc-L-Ile-OH) and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling of Nα-Fmoc-N(in)-Boc-L-tryptophan (Fmoc-L-Trp(Boc)-

OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). Then, Fmoc-L-glutamic acid 5-tert-butyl ester (Fmoc-L-Glu(tBu)-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 18. The compound is purified using reverse-phase chromatography.

Comparative Example 19

(2S)-1-[(2S)-2-acetamido-5-amino-5-oxo-pentanoyl]-N-[(1S)-1-(hydroxycarbamoyl)-2-methylbutyl]pyrrolidine-2-carboxamide

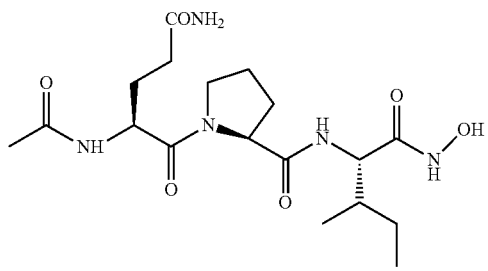 [SMILES: CCC(C)[C@H](NC(=O)[C@@H]1CCCN1C(=O)[C@H](CCC(N)=O)NC(C)=O)C(=O)NO]

0.8 eq of commercially available Fmoc-L-isoleucine (Fmoc-L-Ile-OH) and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Fmoc-L-Proline (Fmoc-L-Pro-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). Then, Nα-Fmoc-Nδ-trityl-L-glutamine (Fmoc-L-Gln(Trt)-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test.

For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a $N_2$ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 19. The compound is purified using reverse-phase chromatography.

Comparative Example 20

(2S)-2-[[(2S)-1-acetylpyrrolidine-2-carbonyl]-methyl-amino]-N-[(1S)-2-(hydroxyamino)-1-(1H-indol-3-ylmethyl)-2-oxo-ethyl]pentanediamide

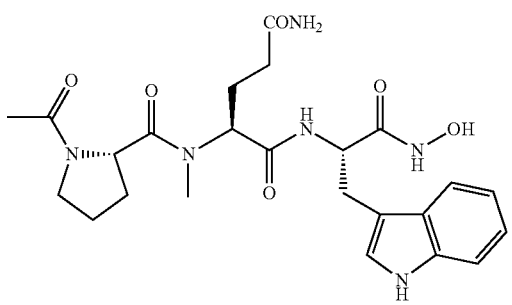 [SMILES: CC(=O)N1CCC[C@H]1C(=O)N(C)[C@@H](CCC(N)=O)C(=O)N[C@@H](Cc1c[nH]c2ccccc12)C(=O)NO]

0.8 eq of commercially available Nα-Fmoc-N(in)-Boc-L-tryptophan (Fmoc-L-Trp(Boc)-OH), and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Nα-Fmoc-Nδ-trityl-L-glutamine (Fmoc-L-Gln(Trt)-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). For the N-methylation of the amino group of the Gln moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencenesulfonate in DMF for 30 minutes (3 treatments). Between treatments the resin is washed thoroughly with DMF and DCM. After the N-methylation of the Gln amino group, the ortho-nitro benzene sulfonyl protecting group is removed by treating the resin with 10 eq of 13-mercaptoethanol and 5 eq of DBU (1×10' and 1×40'). The removal of the ortho-nitro benzene sulfonyl group is assessed using the chloranil test. Then, Fmoc-L-Proline (Fmoc-L-Pro-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a N2 atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5: 2.5) is added to the peptide crude and the mixture is lightly stirred during 2 hours. Afterwards, TFA is evaporated under a $N_2$ flow, yielding example 20. The compound is purified using reverse-phase chromatography.

Comparative Example 21

(2S)-1-acetyl-N-[(1S)-1-[[(1S)-2-(hydroxyamino)-1-(1H-indol-3-ylmethyl)-2-oxo-ethyl]carbamoyl]-2-methyl-butyl]-N-methyl-pyrrolidine-2-carboxamide

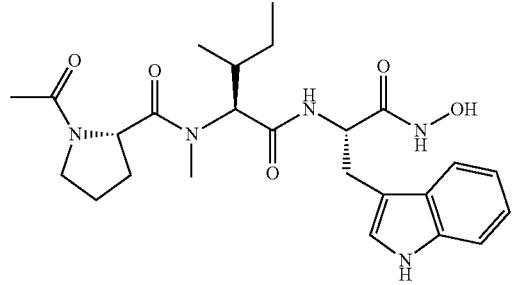 [SMILES: CCC(C)[C@@H](C(=O)N[C@@H](Cc1c[nH]c2ccccc12)C(=O)NO)N(C)C(=O)[C@@H]1CCCN1C(C)=O]

0.8 eq of commercially available Nα-Fmoc-N(in)-Boc-L-tryptophan (Fmoc-L-Trp(Boc)-OH), and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Nα-Fmoc-L-Isoleucine (Fmoc-L-Ile-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). For the N-methylation of the amino group of the Ile moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencenesulfonate in DMF for 30 minutes (3 treatments). Between treatments the resin is washed thoroughly with DMF and 5 DCM. After the N-methylation of the Ile amino group, the ortho-nitro benzene sulfonyl protecting group is removed by treating the resin with 10 eq of β-mercaptoethanol and 5 eq of DBU (1×10' and 1×40'). The removal of the ortho-nitro benzene sulfonyl group is assessed using the chloranil test. Then, Fmoc-L-Proline (Fmoc-L-Pro-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the acetylation of the N-part terminal part of the peptide, 20 eq of acetic anhydride and 20 eq of DIEA are added to the resin. The mixture is allowed to react for 30 minutes and the extent of the reaction is monitored using the chloranil test. For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a N₂ atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a N₂ flow, yielding example 21. The compound is purified using reverse-phase chromatography.

Comparative Example 22

(2S)—N-[(1S)-1-[[(1S)-2-(hydroxyamino)-1-(1H-indol-3-ylmethyl)-2-oxo-ethyl]carbamoyl]-2-methyl-butyl]-N-methyl-1-tetradecanoyl-pyrrolidine-2-carboxamide

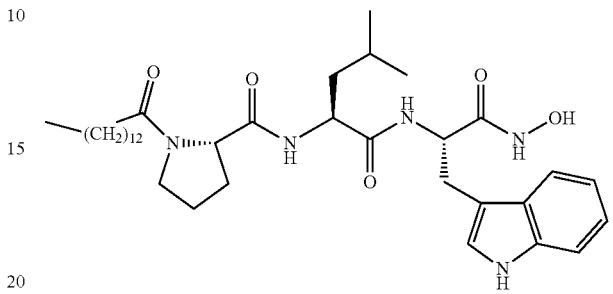

0.8 eq of commercially available Nα-Fmoc-N(in)-Boc-L-tryptophan (Fmoc-L-Trp(Boc)-OH), and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Fmoc-L-Leucine (Fmoc-L-Leu-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). Then, Fmoc-L-Proline (Fmoc-L-Pro-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the capping of the N-part terminal part of the peptide, 3 eq of myristyl acid, 3 eq of the coupling agent TBTU and 6 eq of DIEA are added to the resin. The mixture is allowed to react for 60 minutes and the extent of the reaction is monitored using 15 the chloranil test. For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2,4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a N2 atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5: 2.5) is added to the peptide crude and the mixture is lightly stirred during 2 hours. Afterwards, TFA is evaporated under a $N_2$ flow, yielding example 22. The compound is purified using reverse-phase chromatography.

Comparative Example 23

(2S)-2-[[(SS)-1-hexanoylpyrrolidine-2-carbonyl)-methyl-amino]-N-[(1S)-2-(hydroxyamino)-1-(1H-indol-3-ylmethyl)-2-oxo-ethyl]pentanediamide

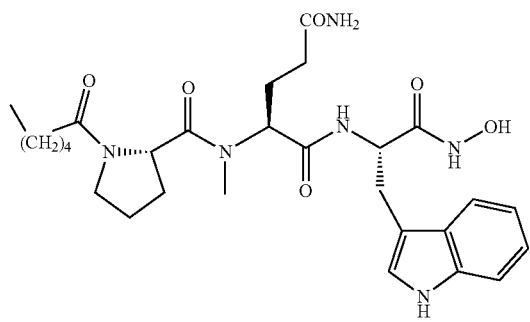

0.8 eq of commercially available Nα-Fmoc-N(in)-Boc-L-tryptophan (Fmoc-L-Trp(Boc)-OH), and DIEA (4 eq) are added to the resin in 2 mL DMF. The mixture is intermittently stirred manually during 1 hour. After that, 0.5 mL/g of MeOH are added to the reaction 10 mixture to cap the remaining reactive points of resin. After 15 minutes, the solution is filtered off and the resin is washed thoroughly with DCM, DMF and MeOH. Fmoc removal is achieved by treating the resin with 20% piperidine in DMF (1×5', 1×10' and 1×15'). For the coupling Nα-Fmoc-Nδ-trityl-L-glutamine (Fmoc-L-Gln(Trt)-OH), 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. To extent of the reaction is monitored using the Kaiser test. The Fmoc group is then removed by treatments with 20% piperidine in DMF (1×5', 1×10'). For the N-methylation of the amino group of the Gln moiety, the free amino group is protected with ortho-nitro benzene sulfonyl chloride (4 eq) using collidine (10 eq) as a base in DMF, which are allowed to react with the resin for 30 minutes. Then, the resin is rinsed with DMF and DCM, and the protection step is repeated again under the same conditions. The extent of the protection is monitored using the Kaiser test. The N-methylation of the amino group is achieved by treating the resin with 3 eq of 7-methyl-1,5,7-triazabicyclo[4.4.0]dec-5-ene and 4 eq of para-nitrobencenesulfonate in DMF for 30 minutes (3 treatments). Between treatments the resin is washed thoroughly with DMF and DCM. After the N-methylation of the Gln amino group, the ortho-nitro benzene sulfonyl protecting group is removed by treating the resin with 10 eq of 3-mercaptoethanol and 5 eq of DBU (1×10' and 1×40'). The removal of the ortho-nitro benzene sulfonyl group is assessed using the chloranil test. Then, Fmoc-L-Proline (Fmoc-L-Pro-OH) is attached, for that purpose 3 eq of the amino acid, 3 eq of the coupling agent TBTU and 6 eq of DIEA dissolved in a small amount of DMF and premixed for 2 minutes. After which, the mixture is added to the resin and the reaction is allowed to react for 90 minutes. The extent of the reaction is monitored using the Kaiser test. The Fmoc group is then 10 removed by treatments with 20% piperidine in DMF (1×5', 1×10' and 1×15') and additional treatment with a mixture of piperidine/DBU/toluene/DMF (5:5:20:70) (1×5'). For the capping of the N-part terminal part of the peptide, 3 eq of hexanoic acid, 3 eq of the coupling agent TBTU and 6 eq of DIEA are added to the resin. The mixture is allowed to react for 60 minutes and the extent of the reaction is monitored using the chloranil test. For the cleavage of the peptide, the resin is washed several times with DCM and dried by suction. The linear side-chain protected peptide is cleaved from the resin by adding a solution of HFIP/DCM (1:4), the mixture is allowed to react for 15 min. Then the reaction mixture is filtered and the resin rinsed with 30 HFIP/DCM. This cleavage procedure is repeated for a second time. All the filtrates are pooled and the solvent is evaporated under vacuum. The crude peptide is used for the formation of the hydroxamide in solution without prior purification. The peptide is dissolved in DCM. After which, 3.5 eq of O-(2, 4-dimethoxybenzyl)hydroxylamine, 5 eq of 4-methylmorpholine, 1.3 eq of the 5 coupling agent EDC.HCl and 1.3 eq of the additive HOAt are added and the mixture is allowed to react under a N2 atmosphere overnight. The extent of the reaction is monitored using HPLC. Once the desired product is obtained, the mixture is washed with 1N HCl, water and brine. The organic layer is dried over magnesium sulfate, filtered and evaporated. After that, a mixture of TFA/water/TIS (95:2.5:2.5) is added to the peptide crude and the mixture is lightly stirred during 2 hours. Afterwards, TFA is evaporated under a $N_2$ flow, yielding example 23. The compound is purified using reverse-phase chromatography.

Experiments

Determination of Inhibitory Effect of Novel Compounds on Matrix MMP-2 and MMP-9

General Considerations:

All the experiments were done in 1× reaction buffer, which was obtained from a 10× reaction buffer solution. The content of the 10× reaction buffer was: 50 mL of 0.5 M Tris-HCl, 1.5 M NaCl, 50 mM $CaCl_2$ and 2 mM sodium azide at pH 7.6. To obtain the 1× reaction buffer 4 mL of the 10× reaction buffer were diluted in 36 mL of $H_2O$.

MMP-2 Inhibition Assay:

Recombinant MMP-2 expressed in Chinese hamster ovary (CHO) cells was obtained from Merck-Millipore (catalog number PF023-5UG). DQ gelatin from pig skin fluorescein conjugated (MMP-2 substrate) was obtained from Life Technologies (catalog number E12055).

Preparation of the MMP-2 for the activity assay: MMP-2 was provided as a stock solution (0.1 mg/mL). The enzyme was diluted in 1× reaction buffer to a final concentration of 5 μg/mL.

Preparation of the DQ gelatin (substrate) solution for the activity assay: the solid form of the substrate was dissolved in water in order to obtain a stock solution of 1 mg/mL.

Procedure: The enzymatic assays were performed in 96-well microtiter plate, which allowed simultaneous monitoring of multiple reactions. For each reaction, 86.3 μL of 1× reaction buffer (pH 7.6), 1.7 μL of MMP-2 (final concentration 85 ng/mL) and 2 μL of the corresponding new compound were added to each well. A stock solution of new compound was prepared in DMSO (100 mM), and dilutions were prepared from this stock solution with DMSO. Finally, to the mixture contained in each well 10 μL of the substrate were added (final concentration 50 μg/mL). The reaction was incubated for 2 hours at room temperature in an orbital shaker (100 rpm).

The inhibitory activity of the new compound was measured fluorimetrically. The excitation and emission wavelengths were 483 and 525 nm, respectively.

MMP-9 Inhibition Assay:

Recombinant MMP-9 expressed was obtained from Merck-Millipore (catalog number PF140-5UG, used in examples 1 to 9 and comparative examples) and Enzo (catalog number-SE360-0010, used in examples 10 to 16). DQ gelatin from pig skin fluorescein conjugated (MMP-9 substrate) was obtained from Life Technologies (catalog number E12055).

Preparation of the MMP-9 for the activity assay: MMP-9 was provided as a stock solution (0.1 mg/mL). The enzyme was diluted in 1× reaction buffer to a final concentration of 5 μg/mL.

Preparation of the DQ gelatin (substrate) solution for the activity assay: the solid form of the substrate was dissolved in water in order to obtain a stock solution of 1 mg/mL.

Procedure: The enzymatic assays were performed in 96-well microtiter plate, which allowed simultaneous monitoring of multiple reactions. For each reaction, 84.6 μL of 1× reaction buffer (pH 7.6), 3.4 μL of MMP-9 (final concentration 85 ng/mL) and 2 μL of the corresponding new compound were added to each well. A stock solution of new compound was prepared in DMSO (100 mM), and dilutions were prepared from this stock solution with DMSO. Finally, to the mixture contained in each well 10 μL of the substrate were added (final concentration 50 μg/mL). The reaction was incubated for 4 hours at room temperature in an orbital shaker (100 rpm).

The inhibitory activity of the new compound was measured fluorimetrically. The excitation and emission wavelengths were 483 and 525 nm, respectively.

Inhibitory activity at several concentration points (ranging from 100 pM to 200 μM MMP) were measured for each compound. The inhibitory activity on MMP-2 and MMP-9 was calculated according to eq 1. For each new compound, the fluorescence in the presence (a) and in the absence (b) of the corresponding MMP was measured. The maximum fluorescence (0% inhibitory activity) was obtained from a sample of the corresponding MMP in the absence of inhibitory compounds. To estimate the inhibitory potency of the novel compounds, activities were plotted against the log concentration of the compound, adjusting to a sigmoid curve using GraphPad Prism software, and the IC$_{50}$ value, defined as the concentration of compound required to inhibit 50% of the corresponding MMP activity, was determined from resulting curve.

$$\text{Inhibitory activity (\%)} = \left[1 - \left(\frac{a-b}{c-d}\right)\right] \times 100 \quad \text{(Equation 1)}$$

wherein:
a corresponds to fluorescence intensity in the presence of substrate+test compound+MMP
b corresponds to the fluorescence intensity in the presence of substrate+tested compound
c corresponds to the fluorescence intensity in the presence of substrate+MMP
d corresponds to the fluorescence intensity of the presence of substrate The new compounds showed high inhibition potency against MMP-2 and MMP-9. The results are summarized in table 1.

TABLE 1

Inhibition of MMP-2 and MMP-9

| Compound (Example n°) | MMP-2 IC$_{50}$ (nM) | MMP-9 IC$_{50}$ (nM) |
|---|---|---|
| 1 | 202 | 1260 |
| 2 | 242 | 301 |
| 3 | 81 | 395 |
| 4 | 62 | 235 |
| 5 | 116 | 601 |
| 6 | 400 | 733 |
| 7 | 159 | 713 |
| 8 | 974 | 263 |
| 9 | 362 | 506 |
| 10 | 37 | 223 |
| 11 | 174 | 71 |
| 12 | 21 | 136 |
| 13 | 1149 | 339 |
| 14 | 116 | 46 |
| 15 | 285 | 702 |
| 16 | <1 | 10 |
| C17 | $1.1 \cdot 10^5$ | $3.5 \cdot 10^6$ |
| C18 | $7.1 \cdot 10^5$ | $2.4 \cdot 10^5$ |
| C19 | $>2 \cdot 10^6$ | $>2 \cdot 10^6$ |
| C20 | $5.3 \cdot 10^4$ | $2.2 \cdot 10^4$ |
| C21 | $1.1 \cdot 10^5$ | $1.6 \cdot 10^4$ |
| C22 | $4.8 \cdot 10^3$ | $1.2 \cdot 10^3$ |
| C23 | $>2 \cdot 10^6$ | $>1 \cdot 10^6$ |

Inhibitory Activity Against Related MMP-2 and MMP-9 Proteases: MMP-1, MMP-3 and MMP-7 Inhibition Assays General Considerations:

All the experiments were done in 1× reaction buffer, which was obtained from a 10× reaction buffer solution. The content of the 10× reaction buffer was: 50 mL of 0.5 M Tris-HCl, 1.5 M NaCl, 50 mM CaCl$_2$ and 2 mM sodium azide at pH 7.6. To obtain the 1× reaction buffer 4 mL of the 10× reaction buffer were diluted in 36 mL of H$_2$O.

MMP-1 Inhibition Assay:

Recombinant MMP-1 expressed in *E. Coli* was obtained from Enzo Life Sciences (catalog number BML-SE180). Mca-PLGL-Dpa-AR-NH$_2$ (fluorogenic peptide substrate) was obtained from R&D Systems (catalog number ES001).

Preparation of the MMP-1 for the activity assay: MMP-1 was provided as a stock solution (0.55 mg/mL). The enzyme was diluted in 1× reaction buffer to a final concentration of 276 nM.

MMP-1 peptide substrate was provided as a stock solution in DMSO (6 mM). For the assay, the substrate was diluted 1× reaction buffer to a concentration of 100 μM.

Procedure: The enzymatic assays were performed in 96-well microtiter plate, which allowed simultaneous monitoring of multiple reactions. For each reaction, 86 μL of 1× reaction buffer (pH 7.6), 2 μL of MMP-1 (final concentration 5.52 nM) and 2 μL of the corresponding new compound were added to each well. A stock solution of the new compound was prepared in DMSO (100 mM), and dilutions were prepared from this stock solution with DMSO. Finally, to the mixture contained in each well 10 μL of the substrate were added (final concentration 10 μM). The reaction was incubated for 4 hours at room temperature in an orbital shaker (100 rpm).

The inhibitory activity of the new compound was measured fluorimetrically. The excitation and emission wavelengths were 320 and 405 nm, respectively.

MMP-3 Inhibition Assay:

Recombinant MMP-3 expressed in *E. Coli* was obtained from Merck-Millipore (catalog number 44217). Mca-RPK-PVE-Nval-WRK(Dnp)-NH$_2$ (fluorogenic peptide substrate) was obtained from R&D Systems (catalog number ES002).

Preparation of the MMP-3 for the activity assay: MMP-3 was provided as a stock solution (0.1 mg/mL). The enzyme was diluted in water to a final concentration of 0.005 mg/mL.

MMP-3 peptide substrate was provided as a stock solution in DMSO (4.5 mM). For the assay, the substrate was diluted 1× reaction buffer to a concentration of 100 μM.

Procedure: The enzymatic assays were performed in 96-well microtiter plate, which allowed simultaneous monitoring of multiple reactions. For each reaction, 84.6 μL of 1× reaction buffer (pH 7.6), 3.4 μL of MMP-3 (final concentration 7.7 nM) and 2 μL of the corresponding new compound were added to each well. A stock solution of new compound was prepared in DMSO (100 mM), and dilutions were prepared from this stock solution with DMSO. Finally, to the mixture contained in each well 10 μL of the substrate were added (final concentration 10 μM). The reaction was incubated for 4 hours at room temperature in an orbital shaker (90 rpm).

The inhibitory activity of the new compound was measured fluorimetrically. The excitation and emission wavelengths were 320 and 405 nm, respectively.

MMP-7 Inhibition Assay:

Recombinant MMP-7 expressed in *E. Coli* was obtained from Merck-Millipore (catalog number 44270). Mca-PLGL-Dpa-AR-NH$_2$ (fluorogenic peptide substrate) was obtained from R&D Systems (catalog number ES001).

Preparation of the MMP-7 for the activity assay: MMP-7 was provided as a stock solution (2.1 mg/mL). The enzyme was diluted in water to a final concentration of 0.005 mg/mL.

MMP-7 peptide substrate was provided as a solid (1 mg). A 4 mM stock solution of the substrate in DMSO was obtained by adding 214.7 μL of DMSO. After which, a 100 μM solution of substrate was prepared in 1× reaction buffer.

Procedure: The enzymatic assays were performed in 96-well microtiter plate, which allowed simultaneous monitoring of multiple reactions. For each reaction, 84.6 μL of 1× reaction buffer (pH 7.6), 3.4 μL of MMP-7 (final concentration 8.3 nM) and 2 μL of the corresponding new compound were added to each well. A stock solution of new compound was prepared in DMSO (100 mM), and dilutions were prepared from this stock solution with DMSO. Finally, to the mixture contained in each well 10 μL of the substrate were added (final concentration 10 μM). The reaction was incubated for 4 hours at room temperature in an orbital shaker (90 rpm).

The inhibitory activity of the new compound was measured fluorimetrically. The excitation and emission wavelengths were 320 and 405 nm, respectively.

Inhibitory activity at several concentration points (1, 10, 100 and 200 μM) were measured for each compound. The inhibitory activity on MMP-1, MMP-3 and MMP-7 was calculated according to eq 1 and The IC$_{50}$ value was calculated as explained above for MMP-2 and MMP-9.

IC$_{50}$ values are shown in table 2.

TABLE 2

IC$_{50}$ over MMP-1, MMP-3 and MMP-7.

| Compound (Example n°) | MMP-1 IC$_{50}$ (nM) | MMP-3 IC$_{50}$ (nM) | MMP-7 IC$_{50}$ (nM) |
|---|---|---|---|
| 1 | $<1 \cdot 10^3$ | $3.01 \cdot 10^7$ | $2.3 \cdot 10^7$ |
| 2 | $4.94 \cdot 10^6$ | $1.92 \cdot 10^7$ | $3.14 \cdot 10^7$ |
| 3 | $6.82 \cdot 10^6$ | $2.54 \cdot 10^7$ | $6.61 \cdot 10^6$ |
| 4 | $4.73 \cdot 10^6$ | $1.33 \cdot 10^7$ | $4.42 \cdot 10^6$ |
| 5 | $6.68 \cdot 10^6$ | $2.57 \cdot 10^7$ | $3.48 \cdot 10^6$ |
| 6 | $2.56 \cdot 10^7$ | $5.34 \cdot 10^7$ | $5.26 \cdot 10^7$ |
| 7 | $2.47 \cdot 10^7$ | $2.25 \cdot 10^7$ | $7.71 \cdot 10^6$ |
| 8 | $3.65 \cdot 10^6$ | $3.81 \cdot 10^6$ | $4.10 \cdot 10^6$ |
| 9 | $1.14 \cdot 10^7$ | $3.20 \cdot 10^6$ | $4.03 \cdot 10^7$ |
| 10 | $6.61 \cdot 10^6$ | $1.60 \cdot 10^8$ | $8.08 \cdot 10^6$ |
| 11 | $9.13 \cdot 10^6$ | $2.00 \cdot 10^8$ | $2.01 \cdot 10^7$ |
| 12 | $1.49 \cdot 10^7$ | $1.57 \cdot 10^8$ | $1.41 \cdot 10^7$ |
| 13 | $2.00 \cdot 10^8$ | $2.00 \cdot 10^8$ | $5.04 \cdot 10^7$ |
| 14 | $6.07 \cdot 10^6$ | $<1.00 \cdot 10^3$ | $6.10 \cdot 10^7$ |
| 15 | $1.08 \cdot 10^7$ | $9.89 \cdot 10^6$ | $4.12 \cdot 10^7$ |
| 16 | $<1.00 \cdot 10^3$ | $<1.00 \cdot 10^3$ | $1.00 \cdot 10^6$ |
| C17 | $6.10 \cdot 10^3$ | $3.1 \cdot 10^3$ | $>2 \cdot 10^6$ |
| C18 | — | — | — |
| C19 | — | — | — |
| C20 | $>2 \cdot 10^6$ | $>2 \cdot 10^6$ | $>2 \cdot 10^6$ |
| C21 | — | — | — |
| C22 | — | — | — |
| C23 | — | — | — |
| C24 | — | — | — |

As may be easily seen when comparing the values of table 2 (showing IC$_{50}$ for MMP-1, MMP-3 and MMP-7) with those of table 1 (showing IC$_{50}$ for MMP-2 and MMP-9), the compounds of the invention are highly selective for MMP-2 and MMP-9.

Determination of Permeability Properties of the Compounds

Parallel Artificial Membrane Permeability Assay (PAMPA)

Parallel artificial membrane permeability assay (PAMPA) described in Kansy et al., *J. M. Chem.* 1998; 41(7):1007-10 was used here to determine the capacity of compounds to cross the Blood-Brain Barrier (BBB) by passive diffusion (Di L et al., *Eur. J. Med. Chem.* 2003; 38(3):223-32). The effective permeability (Pe) of the compounds was measured at an initial concentration of 200 μM. The buffer solution was prepared from a commercial concentrated one following the manufacturer's instructions. pH was adjusted to 7.4 using a 0.5 M NaOH solution. A stock solution of new compound was prepared in DMSO and diluted with buffer solution to a final 200 μM concentration (0.5% DMSO content). The PAMPA sandwich was separated and each donor well was filled with 200 μM of the compound solution. The acceptor plate was placed into the donor plate, ensuring that the underside of the membrane was in contact with buffer. 4 μL of the mixture of phospholipids (20 mg/ml) in dodecane was added to the filter of each well, and 200 μL of buffer solution was added to the each acceptor well. The plate was covered and incubated at room temperature in a saturated humidity atmosphere for 4 hours under orbital agitation at 100 rpm. After 4 hours, the contents of the acceptor and donor compartments were analyzed by HPLC: 150 μL of each well from the donor plate and 150 μL of each well from the acceptor plate were transferred to HPLC vials, injecting each sample into a reverse-phase C$_{18}$ column (150 mm×4.6 mm×5 μm, 100 Å) (100 μL/injection from the acceptor wells, 10 μL/injection from the donor wells and for t0 references). Transport was also confirmed using mass spectrometry (MALDI-TOF).

The phospholipid mixture used was a porcine polar brain lipid extract, provided by Avanti polar lipids, with the following composition: 12.6% phosphatidylcholine (PC), 33.1% phosphatidylethanolamine (PE), 18.5% phosphatidylserine (PS), 4.1% phosphatidylinositol (PI), 0.8% phosphatidic acid and 30.9% of other compounds.

The effective permeability (Pe) after 4 hours was calculated using equation 2 and the percentage of transport (T %) was calculated using equation 3:

$$Pe = \frac{-218.3}{t} \times \log\left[1 - \frac{2Ca(t)}{Cd(t0)}\right] \times 10^{-6} \text{ cm/s} \quad \text{(Equation 2)}$$

$$T\ \% = \frac{Ca(t)}{Cd(t0)} \times 100 \quad \text{(Equation 3)}$$

Wherein:

t is time (h)

Ca(t) is the compound concentration in the acceptor well at time t

And Cd(t0) is the compound concentration in the donor well at t0.

Based on the indicative Pe values shown in Table 4, the novel compounds show good permeability across the BBB (Table 5).

TABLE 4

Indicative Pe values

| Indicative Pe values (cm/s) | Transport inside CNS |
|---|---|
| Pe ≥4 · $10^{-6}$ | Good |
| 2 · $10^{-6}$ ≤ Pe < 4 · $10^{-6}$ | Moderate |
| Pe <2 · $10^{-6}$ | Low |

TABLE 5

Effective permeability (Pe) and percentage of transport of the new compounds

| Compound (Example n°) | Pe (cm/s) | SD | % T | SD |
|---|---|---|---|---|
| 1 | 9.4 · $10^{-8}$ | 2.4 · $10^{-8}$ | 0.4 | 0.1 |
| 2 | 2.0 · $10^{-7}$ | 3.5 · $10^{-8}$ | 0.8 | 0.1 |
| 3 | 2.3 · $10^{-6}$ | 2 · $10^{-7}$ | 9.3 | 0.6 |
| 4 | 7.4 · $10^{-7}$ | 1.4 · $10^{-7}$ | 3.1 | 0.6 |
| 5 | 1.9 · $10^{-6}$ | 4 · $10^{-7}$ | 7.6 | 1.4 |
| 6 | 3.5 · $10^{-6}$ | 8 · $10^{-7}$ | 14.3 | 2.8 |
| 7 | 11.3 · $10^{-6}$ | 6 · $10^{-8}$ | 19.0 | 0.1 |
| 8 | 4.7 · $10^{-6}$ | 0.4 · $10^{-6}$ | 9.0 | 0.7 |
| 9 | 5.2 · $10^{-6}$ | 3.1 · $10^{-6}$ | 9.9 | 0.5 |
| 10 | 7.6 · $10^{-6}$ | 0.2 · $10^{-6}$ | 13.6 | 0.3 |
| 15 | 1.1 · $10^{-6}$ | 0.1 · $10^{-6}$ | 2.3 | 0.5 |
| 16 | 3.7 · $10^{-6}$ | 0.07 · $10^{-6}$ | 7.3 | 0.1 |

The invention claimed is:

1. A compound of formula (I):

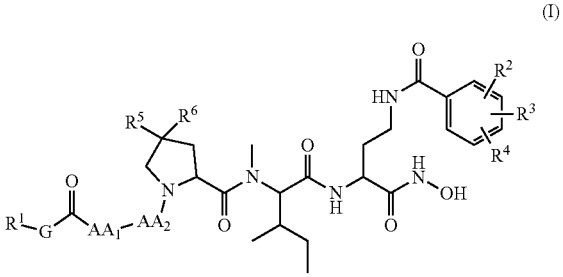

(I)

wherein $AA_1$ is either absent or represents an amino acid selected from the group consisting of N-methyl-phenylalanine, N-methyl-tryptophan, N-methyl-tyrosine and N-methyl-isoleucine, $AA_2$ is either absent or represents an amino acid selected from the group consisting of N-methyl-phenylalanine, N-methyl-alanine, N-methyl-β-alanine and N-methyl-leucine, G is a linear or branched alkylene comprising from 1 to 10 carbon atoms wherein one or more non-vicinal methylene moieties (—$CH_2$—) are optionally replaced by corresponding oxygen atoms (—O—), $R^1$ is selected from the group consisting of hydrogen and phenyl, $R^2$, $R^3$ and $R^4$ are independently selected from the group consisting of hydrogen and fluorine, $R^5$ and $R^6$ are independently selected from the group consisting of hydrogen and fluorine, or a salt thereof.

2. The compound according to claim 1, wherein $AA_1$ and $AA_2$ are absent.

3. The compound according to claim 1, wherein G is selected from the group consisting of —$CH_2$—, —$(CH_2)_3$—, —$(CH_2)_5$—, —$CH_2$—$CH(CH_3)$—$CH_2$—, —$(CH_2)_7$—, —$CH_2$—$CH_2$—$CH_2$—$CH(CH_2$—$CH_2$—$CH_3)$—, —O—$(CH_2)_3$—, —$(CH_2)_{13}$— and —$CH_2$—O—$(CH_2)_2$—O—$CH_2$—.

4. The compound according to claim 3, wherein $R^1$-G is selected from the group consisting of $CH_3$—$(CH_2)_2$—, $CH_3$—$CH(CH_3)$—$CH_2$—, phenyl-O—$(CH_2)_3$—, $CH_3$—$(CH_2)_6$—, $CH_3$—$(CH_2)_4$— and $CH_3$—$CH_2$—$CH_2$—$CH(CH_3$—$CH_2$—$CH_3)$—.

5. The compound according to claim 1, wherein one of $R^2$, $R^3$ and $R^4$ is hydrogen.

6. The compound according to claim 5, wherein one of $R^2$, $R^3$ and $R^4$ is hydrogen and the other two are fluorine atoms.

7. The compound according to claim 6, wherein the phenyl group substituted by $R^2$, $R^3$ and $R^4$ is a 3,5-difluorophenyl.

8. The compound according to claim 1, wherein $R^5$ and $R^6$ are both hydrogen.

9. The compound according to claim 1 of formula:

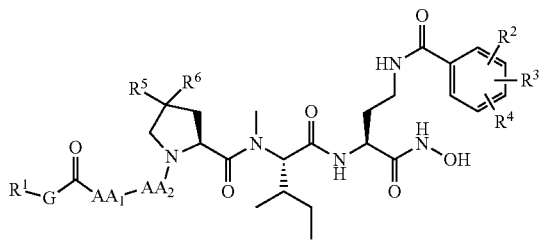

or a salt thereof.

10. The compound according to claim 1 selected from the group consisting of:

(2S)-1-acetyl-N-[(1S)-1-[[(1S)-3-[(4-fluorobenzoyl)amino]-1-(hydroxycarbamoyl)propyl]carbamoyl]-2-methyl-butyl]-N-methyl-pyrrolidine-2-carboxamide (2S)-1-acetyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-1-hexanoyl-N-methyl-pyrrolidine-2-carboxamide (2S)-1-butanoyl-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(3-methylbutanoyl)pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-N-methyl-1-octanoyl-pyrrolidine-2-carboxamide (2S)—N-[(1S,2S)-1-[[(1S)-3-[(3,5-difluorobenzoyl)amino]-1-(hydroxycarbamoyl)propyl]carbamoyl]-2-methyl-butyl]-4,4-difluoro-1-hexanoyl-N-methyl-pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(2-propylpentanoyl)pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-N-methyl-1-(4-phenoxybutanoyl)pyrrolidine-2-carboxamide (2S)—N-[(1S)-1-[[(1S)-3-[(3,5-difluorobenzoyl)amino]-1-(hydroxycarbamoyl)propyl]carbamoyl]-2-methyl-butyl]-4,4-difluoro-N-methyl-1-(4-phenoxybutanoyl)pyrrolidine-2-carboxamide (2S)-1-[(2S)-2-[acetyl(methyl)amino]-3-phenyl-butanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide (2S)-1-[(2S)-2-[acetyl(methyl)amino]propanoyl]-N-[(1S)-1-[[(1 S)-3-[(3,5-difluorobenzoyl)amino]-1-(hydroxycarbamoyl)propyl]carbamoyl]-2-methyl-butyl]-N-methyl-pyrrolidine-2-carboxamide (2S)-1-[3-[acetyl(methyl)amino]propanoyl]-N-[(1S)-1-[[(1S)-3-[(3,5-difluorobenzoyl)amino]-1-(hydroxycarbamoyl)propyl]carbamoyl]-2-methyl-butyl]-N-methyl-pyrrolidine-2-carboxamide (2S)-1-[(2S)-2-[[2-[butanoyl(methyl)amino]-3-(1H-indol-3-yl)propanoyl]-methyl-amino]-4-methyl-pentanoyl]-N-[(1S)-1-[[(1 S)-3-[(3,5-difluorobenzoyl)amino]-1-(hydroxycarbamoyl)propyl]carbamoyl]-2-methyl-butyl]-N-methyl-pyrrolidine-2-carboxamide (2S)—N-[(1S)-1-[[(1S)-3-benzamido-1-(hydroxycarbamoyl)propyl]carbamoyl]-2-methyl-butyl]-N-methyl-1-hexanoyl-pyrrolidine-2-carboxamide (2S,4R)—N-[(1S)-1-[[(1S)-3-benzamido-1-(hydroxycarbamoyl)propyl]carbamoyl]-2-methyl-butyl]-4-fluoro-N-methyl-1-pentanoyl-pyrrolidine-2-carboxamide or a pharmaceutically acceptable salt, or isomer thereof.

11. Pharmaceutical compositions comprising a compound according to claim 1 and a pharmaceutically acceptable carrier, adjuvant or vehicle.

12. A method for treatment of epilepsy, schizophrenia, Alzheimer disease, autism, mental retardation, bipolar disorders, mood disorders depression, vascular diseases, inflammatory diseases, drug addiction, neuropathic pain, lung diseases, cancer and sepsis wherein a therapeutic amount of the compound according to claim 1 is administered to a patient in need of said treatment.

13. The method of claim 12, wherein the autism is associated to fragile X syndrome.

14. The method of claim 12, wherein the mood disorders are bipolar disorders.

15. The method of claim 12, wherein the vascular diseases are selected from the group consisting of ischemic stroke and atherosclerosis.

16. The method of claim 12, wherein the inflammatory diseases are selected from the group consisting of multiple sclerosis, rheumatoid arthritis, and inflammatory bowel disease.

17. The method of claim 12, wherein the lung diseases are selected from the group consisting of asthma and chronic obstructive pulmonary disease.

* * * * *